(12) United States Patent
Johannaber et al.

(10) Patent No.: US 10,792,162 B2
(45) Date of Patent: Oct. 6, 2020

(54) SHOULDER ARTHROPLASTY TRIAL SENSORS

(71) Applicant: Zimmer, Inc., Warsaw, IN (US)

(72) Inventors: Kenneth D. Johannaber, Reno, NV (US); John Minck, Jr., Reno, NV (US); Rida Hariri, Reno, NV (US); Derek Dalbey, Reno, NV (US)

(73) Assignee: Zimmer, Inc., Warsaw, IN (US)

( * ) Notice: Subject to any disclaimer, the term of this patent is extended or adjusted under 35 U.S.C. 154(b) by 0 days.

(21) Appl. No.: 15/801,025

(22) Filed: Nov. 1, 2017

(65) Prior Publication Data

US 2018/0161168 A1 Jun. 14, 2018

Related U.S. Application Data

(60) Provisional application No. 62/434,210, filed on Dec. 14, 2016.

(51) Int. Cl.
*A61F 2/40* (2006.01)
*A61F 2/46* (2006.01)
(Continued)

(52) U.S. Cl.
CPC ............... *A61F 2/40* (2013.01); *A61B 34/20* (2016.02); *A61F 2/4612* (2013.01);
(Continued)

(58) Field of Classification Search
CPC .... A61B 5/4576; A61F 2/4684; A61F 2/4003; A61F 2002/4018
See application file for complete search history.

(56) References Cited

U.S. PATENT DOCUMENTS 7,300,432 B2  11/2007  Surma et al.
8,167,823 B2   5/2012  Nycz et al.
(Continued)

FOREIGN PATENT DOCUMENTS

CN   110035716 A   7/2019
CN   110049748 A   7/2019
(Continued)

OTHER PUBLICATIONS

"U.S. Appl. No. 15/800,915, Restriction Requirement dated May 2, 2019", 9 pgs.
(Continued)

*Primary Examiner* — David H Willse
*Assistant Examiner* — Javier G Blanco
(74) *Attorney, Agent, or Firm* — Schwegman Lundberg & Woessner, P.A.

(57) ABSTRACT

An arthroplasty trial assembly for a human shoulder can include a first implant securable to a first bone and a second implant securable to a second bone. The second implant can include a body, a stem, an articulation component, and a sensor. The stem can extend from the body, and the stem can be insertable into the second bone. The articulation component can be coupled to the body opposite the stem, and the articulation component can be articulable with the first implant. The sensor can be connected to the articulation component and can be configured to monitor a condition of the second implant and can produce a sensor signal as a function of the condition that is indicative of stability of the shoulder.

10 Claims, 13 Drawing Sheets

(51) Int. Cl.
  *A61B 34/20* (2016.01)
  *A61B 34/10* (2016.01)
  *A61F 2/30* (2006.01)
(52) U.S. Cl.
  CPC .......... *A61F 2/4657* (2013.01); *A61F 2/4684* (2013.01); *A61B 2034/105* (2016.02); *A61B 2034/108* (2016.02); *A61B 2034/2046* (2016.02); *A61F 2/4003* (2013.01); *A61F 2002/30566* (2013.01); *A61F 2002/4018* (2013.01); *A61F 2002/4658* (2013.01); *A61F 2002/4666* (2013.01)

(56) References Cited

U.S. PATENT DOCUMENTS

| | | | |
|---|---|---|---|
| 8,393,409 | B2 | 3/2013 | Pedicini |
| 8,695,726 | B2 | 4/2014 | Pedicini |
| 9,414,940 | B2 | 8/2016 | Stein et al. |
| 10,660,760 | B2 | 5/2020 | Johannaber et al. |
| 2002/0101232 | A1 | 8/2002 | Mendes et al. |
| 2004/0243148 | A1 | 12/2004 | Wasielewski |
| 2005/0010301 | A1 | 1/2005 | Disilvestro et al. |
| 2005/0101962 | A1 | 5/2005 | Schwenke et al. |
| 2006/0069447 | A1* | 3/2006 | DiSilvestro ............... A61F 2/36 623/23.16 |
| 2006/0271199 | A1 | 11/2006 | Johnson |
| 2007/0005145 | A1 | 1/2007 | Banks et al. |
| 2007/0149981 | A1 | 6/2007 | Bhattacharyya |
| 2008/0065225 | A1 | 3/2008 | Wasielewski et al. |
| 2010/0217156 | A1 | 8/2010 | Fisher et al. |
| 2010/0331734 | A1 | 12/2010 | Stein |
| 2010/0331737 | A1 | 12/2010 | Stein et al. |
| 2010/0332152 | A1 | 12/2010 | Stein |
| 2011/0093087 | A1 | 4/2011 | Mcmahon et al. |
| 2011/0319755 | A1 | 12/2011 | Stein et al. |
| 2012/0220430 | A1 | 8/2012 | Bucar et al. |
| 2013/0090737 | A1* | 4/2013 | Flaherty ............... A61F 2/30749 623/19.13 |
| 2013/0197656 | A1 | 8/2013 | Conrad |
| 2014/0249535 | A1 | 9/2014 | McCarthy et al. |
| 2014/0330281 | A1 | 11/2014 | Aghazadeh |
| 2015/0018718 | A1 | 1/2015 | Aghazadeh |
| 2015/0196343 | A1 | 7/2015 | Donald et al. |
| 2015/0282856 | A1 | 10/2015 | Haiat et al. |
| 2015/0289890 | A1 | 10/2015 | Chen et al. |
| 2015/0297362 | A1 | 10/2015 | Singh et al. |
| 2016/0029952 | A1 | 2/2016 | Hunter et al. |
| 2017/0007330 | A1* | 1/2017 | Britton ................... A61B 34/10 |
| 2018/0116805 | A1 | 5/2018 | Johannaber et al. |
| 2018/0116821 | A1 | 5/2018 | Johannaber et al. |
| 2018/0116823 | A1 | 5/2018 | Johannaber et al. |

FOREIGN PATENT DOCUMENTS

| | | |
|---|---|---|
| EP | 2335651 | 6/2011 |
| EP | 3058865 | 8/2016 |
| WO | 2013117909 | 8/2013 |
| WO | WO-2014144107 A1 | 9/2014 |
| WO | 2018085417 | 5/2018 |
| WO | 2018085423 | 5/2018 |
| WO | WO 2018/111429 | 6/2018 |

OTHER PUBLICATIONS

"International Application Serial No. PCT/US2017/059552, International Preliminary Report on Patentability dated May 16, 2019", 9 pgs.
"International Application Serial No. PCT/US2017/059559, International Preliminary Report on Patentability dated May 16, 2019", 9 pgs.
U.S. Appl. No. 15/800,915, filed Nov. 1, 2017, Device for Sensing Implant Location and Impingement.
U.S. Appl. No. 15/800,932, filed Nov. 1, 2017, Device for Sensing Implant Location and Impingement.
U.S. Appl. No. 15/800,988, filed Nov. 1, 2017, Impact Force Feedback Display System.
"International Application Serial No. PCT US2017 059552, International Search Report dated Feb. 20, 2018", 4 pgs.
"International Application Serial No. PCT US2017 059552, Written Opinion dated Feb. 20, 2018", 7 pgs.
"International Application Serial No. PCT US2017 059565, International Search Report dated Feb. 26, 2018", 5 pgs.
"International Application Serial No. PCT US2017 059565, Written Opinion dated Feb. 26, 2018", 8 pgs.
"International Application Serial No. PCT US2017 059559, International Search Report dated Mar. 5, 2018", 5 pgs.
"International Application Serial No. PCT US2017 059559, Written Opinion dated Mar. 5, 2018", 9 pgs.
"U.S. Appl. No. 15/800,915, Non Final Office Action dated Aug. 22, 2019", 14 pgs.
"U.S. Appl. No. 15/800,915, Response filed Jul. 1, 2019 to Restriction Requirement dated May 2, 2019", 8 pgs.
"U.S. Appl. No. 15/800,932, Non Final Office Action dated Oct. 31, 2019", 20 pgs.
"U.S. Appl. No. 15/800,932, Response filed Oct. 8, 2019 to Restriction Requirement dated Aug. 8, 2019", 8 pgs.
"U.S. Appl. No. 15/800,932, Restriction Requirement dated Aug. 8, 2019", 8 pgs.
"U.S. Appl. No. 15/800,988, Response filed Nov. 11, 2019 to Restriction Requirement dated Oct. 8, 2019", 7 pgs.
"U.S. Appl. No. 15/800,988, Restriction Requirement dated Oct. 8, 2019", 7 pgs.
"Australia Application Serial No. 2017354043, First Examination Report dated Jun. 27, 2019", 3 pgs.
"Australia Application Serial No. 2017354043, Response filed Jul. 23, 2019 First Examination Report dated Jun. 27, 2019", 8 pgs.
"Canadian Application Serial No. 3,042,672, Response filed Mar. 20, 2020 to Office Action dated Nov. 21, 2019", 11 pages.
"European Application Serial No. 17804724.7, Response to Communication pursuant to Rules 161(1) and 162 EPC filed Feb. 3, 2020", 10 pages.
"Australian Application Serial No. 2019264529, First Examination Report dated Mar. 17, 2020", 4 pages.
"European Application Serial No. 17817317.5, Response to Communication pursuant to Rules 161(1) and 162 EPC filed Jan. 2, 2020", 88 pages.
"Canadian Application Serial No. 3,042,672, Office Action dated Nov. 21, 2019", 3 pages.
"U.S. Appl. No. 15/800,915, Final Office Action dated Jan. 24, 2020", 19 pages.
"U.S. Appl. No. 15/800,932, Response filed Jan. 31, 2020 to Non Final Office Action dated Oct. 31, 2019", 12 pages.
"U.S. Appl. No. 15/800,915, Advisory Action dated Apr. 2, 2020", 4 pages.
"U.S. Appl. No. 15/800,988, Non Final Office Action dated Feb. 20, 2020", 11 pages.
"U.S. Appl. No. 15/800,932, Notice of Allowance dated Mar. 18, 2020", 11 pages.
"U.S. Appl. No. 15/800,915, Response filed Mar. 19, 2020 to Final Office Action dated Jan. 24, 2020", 11 pages.
"U.S. Appl. No. 15/800,915, Response Filed Nov. 22, 2019 to Non-Final Office Action dated Aug. 22, 2019", 11 pages.
U.S. Appl. No. 16/875,408, filed May 15, 2020, Device for Sensing Implant Location and Impingement.
"Canadian Application Serial No. 3,045,624, Office Action dated May 12, 2020", 5 pages.
"U.S. Appl. No. 15/800,988, Response filed May 20, 2020 to Non Final Office Action dated Feb. 20, 2020", 9 pages.

\* cited by examiner

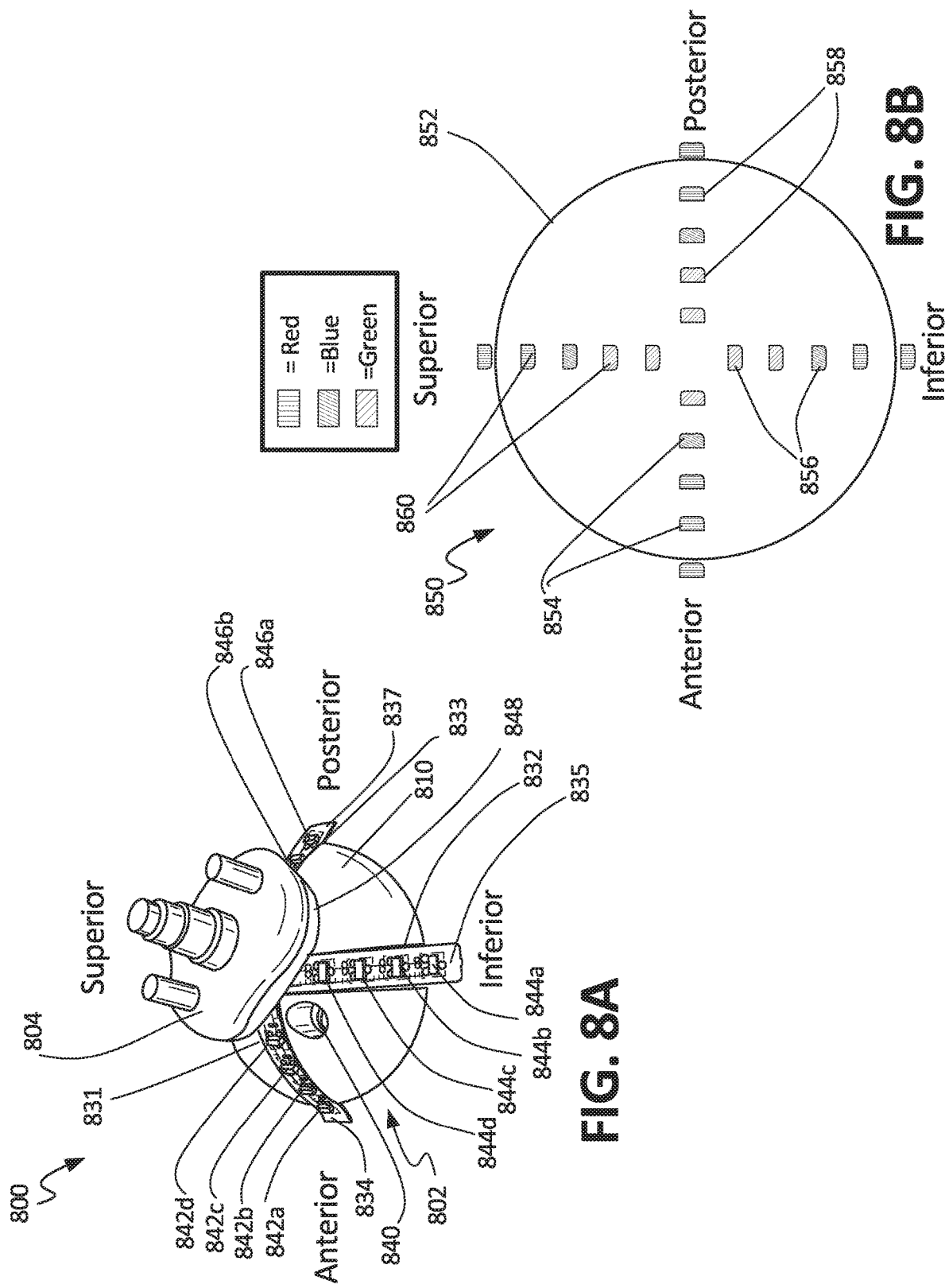

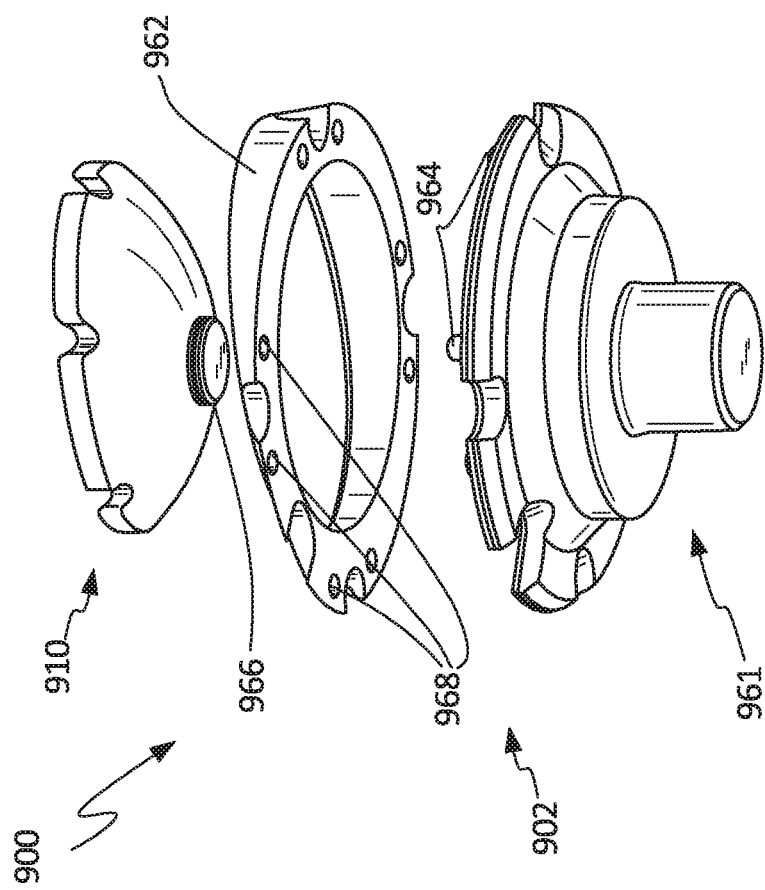
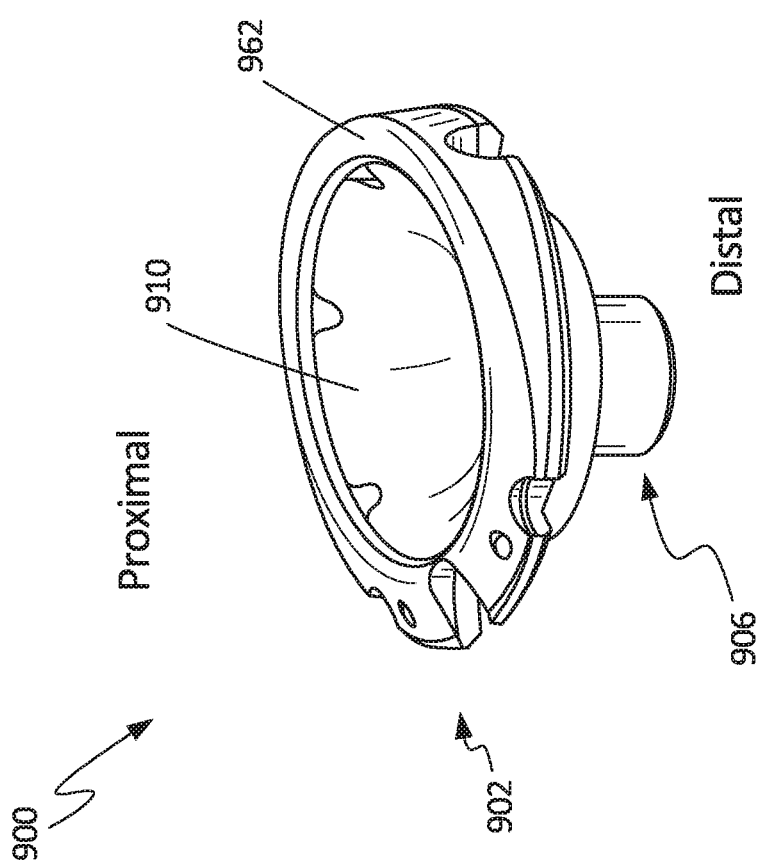
FIG. 9B
FIG. 9A

SHOULDER ARTHROPLASTY TRIAL SENSORS

CLAIM OF PRIORITY

In some examples, rod 322 can include a magnet 323, such as a permanent magnet, disposed on a distal end of rod 322. In these examples, detector 324 can be a sensor configured to produce a sensor signal as a function of a sensed magnetic field, such as a hall sensor, disposed at a distal termination of bore 326 in stem 306. Detector 324 can be disposed in bore 326 in proximity to rod 322 and can be configured to produce a signal as a function of a detected magnetic field emitted by rod 322. In such cases, the displacement signal produce by detector 324 can be correlated to distance d between rod 322 and detector 324. In some other examples, the displacement signal be generated as a function of a sensed electric field, for example when capacitive displacement sensing is used as displacement sensor 318.

FIELD

The present subject matter relates to orthopedic procedures and, more particularly, to assemblies and systems that can aid in performing shoulder arthroplasties.

BACKGROUND

The shoulder joint is a complex joint with the scapula, clavicle and the humerus all coming together to enable a wide range of movement, at least in a properly functioning joint. In a properly functioning shoulder joint the head of the humerus fits into a shallow socket in the scapula, typically referred to as the glenoid. Articulation of the shoulder joint involves movement of the humeral head in the glenoid, with the structure of the mating surfaces and surrounding tissues providing a wide range of motion.

The shoulder joint can undergo degenerative changes caused by various issues, such as rheumatoid arthritis, osteoarthritis, rotator cuff arthroplasty, vascular necrosis, or bone fracture. When severe joint damage occurs and no other means of treatment is found to be effective, a total, partial, or reverse shoulder replacement or reconstruction may be necessary. Total shoulder replacements can involve a humeral prosthetic, including a stem and a head portion used to replace the natural humeral head. Total shoulder replacements will also typically involve resurfacing of the glenoid with a prosthetic implant. The glenoid implant generally will include an articulating cup shaped to receive the prosthetic humeral head. A reversal shoulder replacement (arthroplasty) involves a different set of humeral and glenoid replacement prosthetics. In a reverse shoulder the humeral component includes a cup shaped articular surface attached to a stem implanted into the humerus, while a spherical glenoid component is used to provide an articular surface for the humeral cup.

OVERVIEW

During shoulder arthroplasty surgery, the components of the prosthesis are matched with the bio-kinematics of the patient in an effort to maintain or restore a natural range of motion of a healthy shoulder joint. Patient specific instrumentation can assist a surgeon in planning and implementing a shoulder arthroplasty to restore natural bio-kinematics. However, even with the multitude of advances in prosthetic components and patient specific instrumentation, restoring a full range of motion can remain difficult, especially for a surgeon who does not regularly perform shoulder replacements.

Even current surgical standards are often vague, providing guidance such as joint tension should be 50/50 laxity or the joint should be "stable" throughout the range of motion. It is common for the current surgical standards to use un-quantified subjective measures, such as if the fit is "too tight," soft tissue releases may be performed. Without significant experience, such guidance is of little practical use in ensuring successful outcomes.

The systems, devices, methods, and instruments discussed herein can provide quantitative measurements to assist surgeons in determining whether trial prosthetic devices may provide a patient with desirable outcomes. Providing quantitative values representative of joint tension and/or range of motion, can allow for development of definitive standards of care that routinely result in successful outcomes. Quantitative measurements of certain parameters critical to providing a functional joint also allow for surgeons to knowingly account to patient specific issues, rather than the present vague "feel" that only the most experienced surgeons are likely to use successfully.

While the above discusses issues and procedures specific to shoulder replacement procedures, discussion of the following systems, devices, methods, and instruments is also applicable for use in other joint replacement procedures, such as total hip arthroplasty (THA) or total knee arthroplasty (TKA).

To further illustrate the apparatuses and systems disclosed herein, the following non-limiting examples are provided:

Example 1 is an arthroplasty trial assembly for a human shoulder comprising: a first implant securable to a first bone; and a second implant securable to a second bone, the second implant comprising: a body; a stem extending from the body, the stem insertable into the second bone; an articulation component coupled to the body opposite the stem, the articulation component articulable with the first implant; and a sensor connected to the articulation component and configured to monitor a condition of the second implant and produce a sensor signal as a function of the condition that is indicative of stability of the shoulder.

In Example 2, the subject matter of Example 1 optionally includes wherein the articulation component is translatable relative to the body and the sensor is configured to produce the sensor signal as a function of a position of the articulation component relative to the body.

In Example 3, the subject matter of any one or more of Examples 1-2 optionally include wherein the sensor is configured to produce the sensor signal as a function of a force applied to the second implant by the first implant.

In Example 4, the subject matter of any one or more of Examples 1-3 optionally include wherein the sensor is disposed on an articulation surface of the articulation component and is configured to produce the sensor signal as a function of the proximity of the first implant to the second implant.

In Example 5, the subject matter of Example 4 optionally includes wherein the sensor is a hall sensor and, wherein the first implant includes a magnet disposed on a contact surface of the first implant, the magnet configured to interact with the hall sensor.

Example 6 is a shoulder arthroplasty trial assembly comprising: a first implant securable to a first bone; and a second implant securable to a second bone, the second implant comprising: a body; a stem extending from the body, the stem insertable into the second bone; an articulation component coupled to the body opposite the stem and translatable relative to the body, the articulation component articulable with the first implant; and a displacement sensor connected to the articulation component and configured to produce a displacement signal as a function of translation of the articulation component relative to the body.

In Example 7, the subject matter of Example 6 optionally includes a biasing element connected to the body and the articulation component, the biasing element configured to bias the translatable surface to an extended position.

In Example 8, the subject matter of Example 7 optionally includes an adapter disposed in a bore of the body and extending from the body away from the bore, the adapter coupleable to the articulating component.

In Example 9, the subject matter of Example 8 optionally includes a rod disposed in the bore and engageable at a first end with the adapter, the rod biased to an extended rod position by the biasing element, and the rod including a magnet disposed at a second end of the rod, the magnet configured to interact with the displacement sensor.

In Example 10, the subject matter of Example 9 optionally includes wherein the sensor produces the signal as a function of the distance between the magnet and the sensor.

In Example 11, the subject matter of any one or more of Examples 7-10 optionally include wherein the second implant further comprises: a cup coupled to the body opposite the stem, wherein the articulation component is disposed within the cup to create a convex articulation surface.

In Example 12, the subject matter of Example 11 optionally includes wherein the biasing element is disposed within the cup and biases the articulation component outwardly from the cup.

In Example 13, the subject matter of Example 12 optionally includes wherein the biasing element is a poly wave spring.

In Example 14, the subject matter of Example 13 optionally includes a rod coupled to the articulation component at a first end of the rod, the rod extending from the articulation component toward the stem, and the rod including a magnet disposed at a second end of the rod, the magnet configured to interact with the displacement sensor.

Example 15 is a shoulder arthroplasty trial assembly comprising: a first implant securable to a first bone; and a second implant securable to a second bone, the second implant comprising: a body; a stem extending from the body and insertable into the second bone; an articulation component connected to the body opposite the stem, the articulation component articulable with the first implant; and a proximity sensor disposed on the articulation component and configured to produce a proximity signal as a function of the proximity of the of the articulation component relative to the first implant.

In Example 16, the subject matter of Example 15 optionally includes a magnet coupled to the first implant and configured to interact with the proximity sensor.

In Example 17, the subject matter of any one or more of Examples 15-16 optionally include wherein the first implant further comprises: a cup articulable with the articulation component, wherein the magnet is disposed around an outer circumference of the cup.

In Example 18, the subject matter of any one or more of Examples 15-17 optionally include a plurality of proximity sensors disposed on a surface of the articulation component.

In Example 19, the subject matter of Example 18 optionally includes wherein the plurality of proximity sensors is disposed in an X pattern on the surface of the articulation component.

In Example 20, the subject matter of any one or more of Examples 15-19 optionally include a force sensor coupled to the articulation component and configured to produce a force signal as a function of a force applied to articulation component by the first implant.

Example 21 is a shoulder arthroplasty trial assembly comprising: a first implant securable to a first bone; and a second implant securable to a second bone, the second implant comprising: a body; a stem extending from the body and insertable into the second bone; an articulation component connected to the body opposite the stem, the articulation component articulable with the first implant; and a force sensor coupled to the articulation component and configured to produce a force signal as a function of a force applied to articulation component by the first implant.

In Example 22, the subject matter of Example 21 optionally includes a cup coupled to the body opposite the stem, wherein the articulation component is disposed within the cup to create a convex articulation surface.

In Example 23, the subject matter of Example 22 optionally includes a protrusion extending from the articulation component and engaging the force sensor enabling transmission of forces from the articulation component to the force sensor.

In Example 24, the subject matter of any one or more of Examples 21-23 optionally include wherein the first insert is a glenoid component, and the second insert is a humeral component.

In Example 25, the subject matter of any one or more of Examples 21-24 optionally include a plurality of proximity sensors disposed on the articulation component and configured to produce a proximity signal as a function of the proximity of the of the articulation component relative to the first implant.

In Example 26, the subject matter of any one or more of Examples 21-25 optionally include plurality of switches disposed proximate a perimeter of the articulation component and configured to produce a switch signal when a force applied to the switch is greater than a threshold force.

In Example 27, the subject matter of any one or more of Examples 21-25 optionally include wherein the switch signal is indicative of impingement between the first implant and the second implant.

Example 28 is a method of producing a display representing a condition of a human shoulder joint during a shoulder arthroplasty, the method comprising: installing a humeral component and a glenoid component on a humerus and a glenoid, respectively, wherein one of the humeral component and the glenoid component comprises a proximity sensor; articulating the humeral component relative to the glenoid component; transmitting proximity sensor signals from the proximity sensor as a result of articulation of the humeral component relative to the glenoid component; receiving the proximity sensor signals at a device; producing a graphic display showing a quantification of the proximity sensor signals; and completing the arthroplasty based on the graphic display.

In Example 29, the subject matter of Example 28 optionally includes wherein one of the humeral component and the glenoid component comprises a force sensor; transmitting force sensor signals from the force sensor as a result of articulation of the humeral component relative to the glenoid component; receiving the force sensor signals at the device; and producing a graphic display showing a quantification of the force sensor signals.

In Example 30, the subject matter of any one or more of Examples 28-29 optionally include wherein one of the humeral component and the glenoid component comprises a displacement sensor; transmitting displacement sensor signals from the displacement sensor as a result of articulation of the humeral component relative to the glenoid component; receiving the displacement sensor signals at the device; and producing a graphic display showing a quantification of the displacement sensor signals.

In Example 31, the system, assembly, or method of any one of or any combination of Examples 1-30 is optionally configured such that all elements or options recited are available to use or select from.

These and other examples and features of the present apparatuses and systems will be set forth in part in the following Detailed Description. This Overview is intended to provide non-limiting examples of the present subject matter—it is not intended to provide an exclusive or exhaustive explanation. The Detailed Description below is included to provide further information about the present apparatuses and methods.

BRIEF DESCRIPTION OF THE DRAWINGS

In the drawings, which are not necessarily drawn to scale, like numerals can describe similar components in different views. Like numerals having different letter suffixes can represent different instances of similar components. The drawings illustrate generally, by way of example, but not by way of limitation, various examples discussed in the present document.

FIG. 8A illustrates an isometric view of an anatomical shoulder prosthetic assembly including a plurality of sensors, in accordance with at least one example of this disclosure.

FIG. 8B illustrates a graphic display produced as a function of the plurality of sensors of the anatomical shoulder prosthetic assembly such as illustrated in FIG. 6, in accordance with at least one example of this disclosure.

FIG. 9A illustrates an isometric view of a reverse shoulder prosthetic assembly, in accordance with at least one example of this disclosure.

FIG. 9B illustrates an exploded view of a reverse shoulder prosthetic assembly, in accordance with at least one example of this disclosure.

DETAILED DESCRIPTION

The present application relates to devices and systems for shoulder replacement procedures, such as a reverse shoulder arthroplasty and total or an anatomical shoulder arthroplasty. Such procedures can include the use of trial components, which are installable prior to installation of the permanent prosthetic components. Trial components can be used to determine fit of the joint, such as the stability of the joint, and can be used to select appropriately sized permanent prosthetic component.

Figure 1:
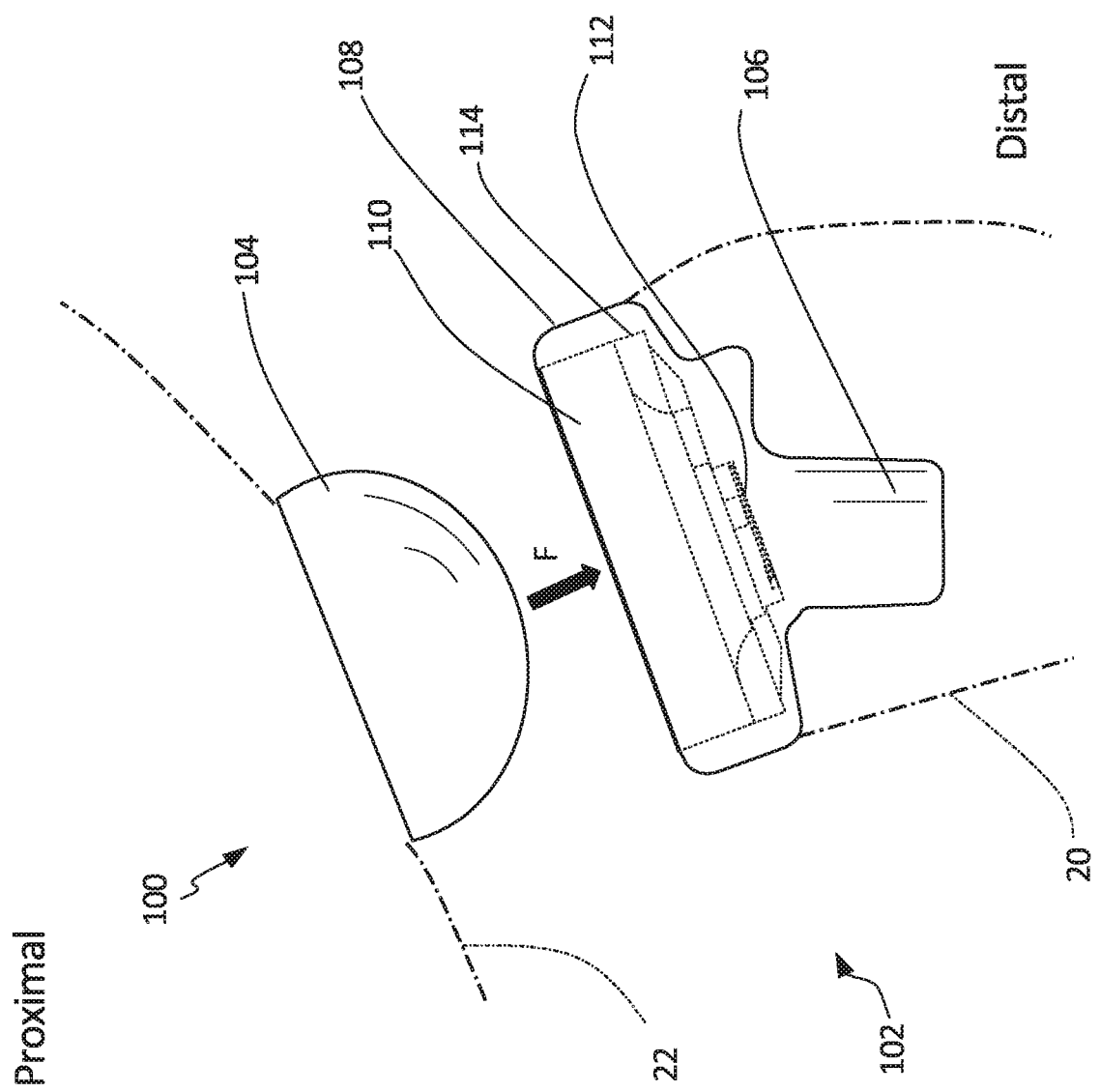
FIG. 1 illustrates an isometric and partial cross-sectional view of a reverse shoulder prosthetic assembly including a sensor, in accordance with at least one example of this disclosure.

FIG. 1 illustrates an isometric view of reverse shoulder 100, which can include humeral component 102 and glenoid component 104. Humeral component 102 can include stem 106, cup 108, articulation surface 110, and force sensor 112. Cup 108 can include bore 114. Also shown in FIG. 1 are humerus 20, glenoid 22, force F, and orientation indicators Proximal and Distal.

Reverse shoulder 100 can be a prosthetic trial assembly for use in a reverse shoulder arthroplasty. Trial assemblies can be used during an arthroplasty procedure to determine sizing and fit of later-installed permanent prosthetic components. Reverse shoulder trial components can involve a humeral component and a glenoid component, such as humeral component 102 and glenoid component 104. Humeral component 102 (or body) can include cup 108 and articulation component 110, where articulation component 110 can be configured to interface with glenoid component 104, providing an articular surface for articulation component 110. In operation of one example, force sensor 112 can measure forces, such as force F, transferred between humeral component 102 and glenoid component 104 and can produce a signal as a function of the measured forces. The signal produced by force sensor 112 can then be used to determined stability of reverse shoulder 100, which can improve the fit of the prosthesis, improving patient quality of life and can improve procedural efficiency, saving cost, in some examples. Further details are discussed below.

Humeral component 102 is an implant configured to be installed on a humerus of a patient. Humeral component 102 can have a generally smooth concave geometry proximally facing glenoid component 104. Humeral component 102 can be a rigid body comprised of materials such as rigid plastics (e.g. polyetherketoneketone), and/or rigid metal alloys (e.g. titanium alloys, stainless alloys, chromium/cobalt alloys, and the like). Glenoid component 104 is an implant configured to be installed on a glenoid of a patient. Glenoid component 104 can be a rigid body comprised of materials such as rigid plastics and/or rigid metal alloys. Glenoid component 104 can have a generally smooth convex geometry distally facing humeral component 102. Glenoid component 104 can have a proximal portion coupleable or securable to glenoid 22.

Stem 106 can extend distally from humeral component 102 and can be configured to engage a bore of humerus 20, to couple or secure humeral component 102 to the humerus of a patient. Cup 108 can be connected to a proximal portion of stem 106 and can have a bore 114 generally forming a concave surface that is proximally facing glenoid component 104. Articulation component 110 can be disposed within cup 108 and can form a generally concave surface at a proximal side of articulation component 110, the surface configured to interface with glenoid component 104. Articulation component 110 can terminate at a distal end where it can engage force sensor 112.

Force sensor 112 can be a sensor configured to produce a signal as a function of a measured force, such as a hydraulic load cell, pneumatic load cell, strain load cell, and the like. Force sensor 112 can be disposed within humeral component 102 to engage articulation component 110 and can include wires that pass through humeral component 102 to connect to an external device. In some examples, force sensor 112 can wirelessly connect to an external device, such as a controller. Wireless connectivity can be provided through protocols such as WiFi, Bluetooth (Bluetooth LE), Near-Field Communications (NFC), and the like.

In operation of one example, glenoid component 104 can be installed on glenoid 22 after preparation of glenoid 22 in a surgical procedure. Humerus 20 can also be prepared to receive humeral component 102, which can be secured to humerus 20 either before or after installation of glenoid component 104 onto glenoid 22. Soft tissues, such as muscles, tendons, and ligaments can also be connected. Then, a physician can operate humerus 20 relative to glenoid 22, allowing glenoid component 104 to articulate on articulation component 110 in an attempt to determine the laxity or stability of the shoulder joint. The physician may move humerus 20 through a pre-determined range of motion or motion profile while monitoring output from the force sensor 112, as discussed further below.

As glenoid component 104 contacts articulation component 110, forces, such as force F, may be transferred between glenoid component 104 and humeral component 102 through articulation component 110. Force F can be measured by force sensor 112, which can produce and transmit a sensor signal as a function of the forces measured by force sensor 112. As discussed further below, the force sensor signal can be analyzed (and visualized through a user interface) to allow for a physician to analyze operation of reverse shoulder 100.

In some examples, the force signal can be used to determine stability of reverse shoulder 100 as it is installed on glenoid 22 and humerus 20. In some examples, a physician can make adjustments to glenoid component 104 and/or humeral component 102 as desired based on the analysis derived from the force signal. In some examples, a physician can use the analysis derived from the force signal of force sensor 112 to select permanent humeral and glenoid prosthetic components. This selection process can improve the fit of the permanent prosthesis, improving patient quality of life and can improve procedural efficiency, saving cost, in some examples.

Figure 2:
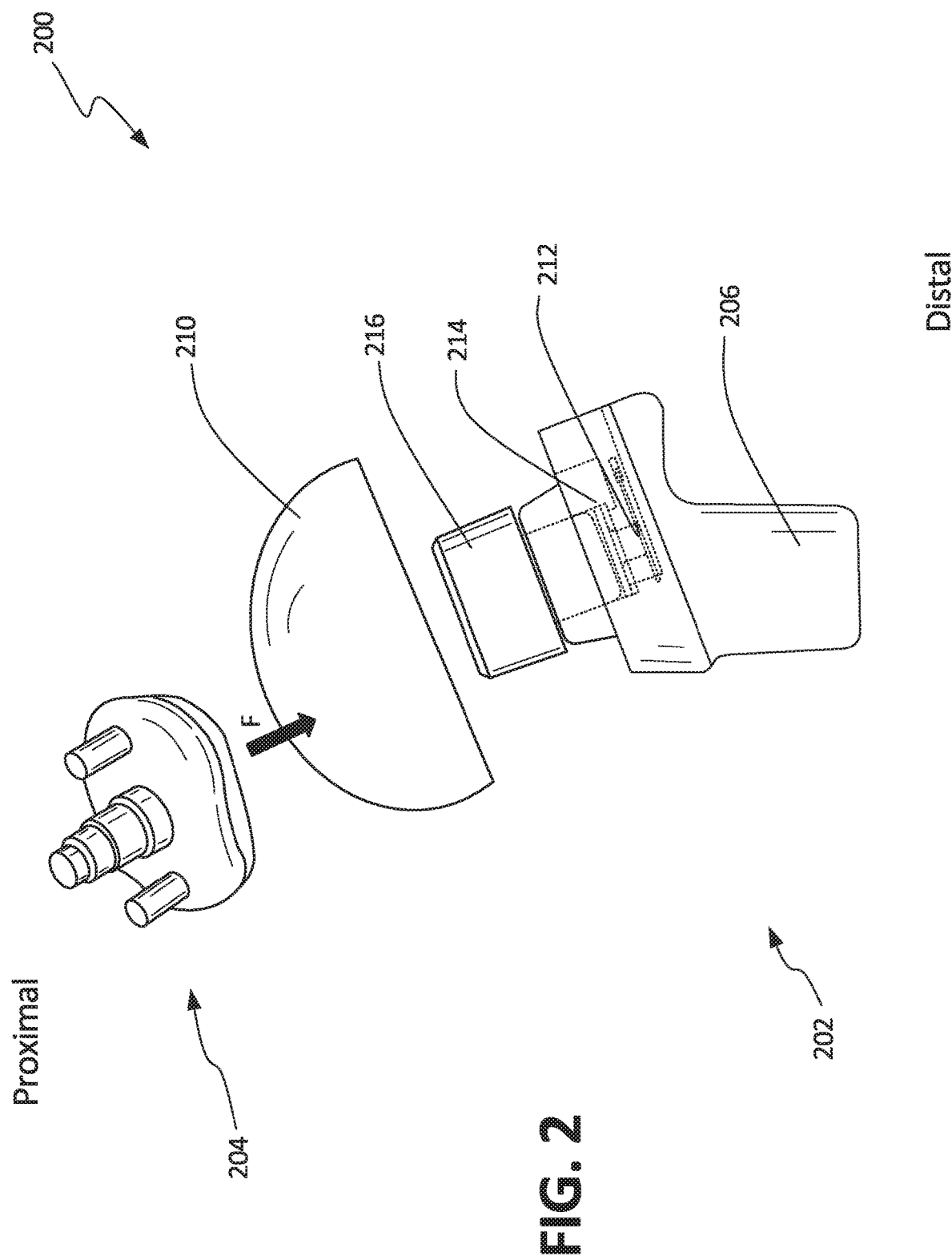
FIG. 2 illustrates an isometric and partial cross-sectional view of an anatomical shoulder prosthetic assembly including a sensor, in accordance with at least one example of this disclosure.

FIG. 2 illustrates an isometric view of anatomical shoulder 200, which can include humeral component 202 and glenoid component 204. Humeral component 202 can include stem 206, articulation component 210, force sensor 212, and adapter 216. Also shown in FIG. 2 are force F and orientation indicators Proximal and Distal.

Anatomical shoulder 200 can be a prosthetic trial assembly for use in an anatomical shoulder arthroplasty. Trial assemblies can be used during an arthroplasty procedure to determine sizing and fit of later-installed permanent prosthetic components. Anatomical (or total) shoulder replacements can involve humeral component 202, which can include stem 206, adapter 216, and articulation component 210 used to replace the natural humeral head. Total shoulder replacements also typically involve resurfacing of the glenoid with a prosthetic implant, such as glenoid component 204. Glenoid component 204 can include an articulating concave surface shaped to receive humeral articulation component 210.

In this example, humeral component 202 is an implant configured to be installed on a humerus of a patient. Humeral component 202 can have a generally smooth convex geometry proximally facing glenoid component 204 (or body). Humeral component 202 can be a rigid body comprised of materials such as rigid plastics (e.g. polyetherketoneketone), and/or rigid metal alloys (e.g. titanium alloys, stainless alloys, chromium/cobalt alloys, and the like). In this example, glenoid component 204 is an implant configured to be installed on a glenoid of a patient. Glenoid component 204 can be a rigid body comprised of materials such as rigid plastics and/or rigid metal alloys. Glenoid component 204 can have a generally smooth concave (or flat, in some examples) geometry distally facing humeral component 202. Glenoid component 204 can have a proximal portion coupleable or securable to a glenoid, such as glenoid 22 of FIG. 1.

Stem 206 can extend distally from humeral component 202 and can be configured to engage a bore of humerus 20, to couple or secure humeral component 202 to the humerus of a patient. Adapter 216 can be connected to a proximal portion of humeral component 202 and generally forming a protrusion facing glenoid component 204. Adapter 216 can terminate at a distal end where it can engage force sensor 212. Adapter 216 can be disposed within bore 214 in a clearance fit manner so that adapter 216 can be removed from bore 214; however, adapter 216 does not translate within bore 214, remaining in constant contact with force sensor 212.

Articulation component 210 can be disposed on and coupled to adapter 216 and can form a generally convex surface configured to interface with glenoid component 204. Because articulation component 210 is not integral to adapter 216, articulation component 210 can be of several sizes or thicknesses. For example, a kit containing humeral component 202 may include articulation components of several sizes or thicknesses. Also, because articulation component 210 is not integral to adapter 216, articulation component 210 can rotate relative to adapter 216, offering greater flexibility to a physician installing the trial components.

Force sensor 212 can be a sensor configured to produce a signal as a function of a measured force, such as a hydraulic load cell, pneumatic load cell, strain load cell, and the like. Force sensor 212 can be disposed within humeral component 202 to engage adapter 216 and can include wires that pass through humeral component 202 to connect to an external device. In some examples, force sensor 212 can wirelessly connect to an external device. A distal end of adapter 216 engages a proximal portion of force sensor 212 when force F is applied to component 210.

In operation of one example, glenoid component 204 can be installed on a glenoid in a surgical procedure and humeral component 202 can be secured to a humerus. Soft tissues, such as muscles, tendons, and ligaments can also be connected. Then, a physician can operate the humerus relative to the glenoid, allowing glenoid component 204 to articulate on articulation component 210.

As glenoid component 204 contacts articulation component 210, forces, such as force F, may be transferred between glenoid component 204 and humeral component 202 through articulation component 210. Force F can be transferred to force sensor 212 by adapter 216. Force sensor 212 can measure the transmitted forces and can produce and transmit a sensor signal as a function of the forces measured by force sensor 212. As discussed further below, the force sensor signal can be analyzed (and visualized through a user interface) to allow for a physician to analyze operation of anatomical shoulder 200. In one example, the force signal can be used to determine stability of anatomical shoulder 200 as it is installed on a glenoid and a humerus. In some examples, a physician can make adjustments to glenoid component 204 and/or humeral component 202 as desired based on the analysis derived from the force signal. In some examples, a physician can use the analysis derived from the force signal of force sensor 212 to select permanent humeral and glenoid prosthetic components. This selection process can improve the fit of the permanent prosthesis, improving patient quality of life and can improve procedural efficiency, saving cost, in some examples.

Figure 3:
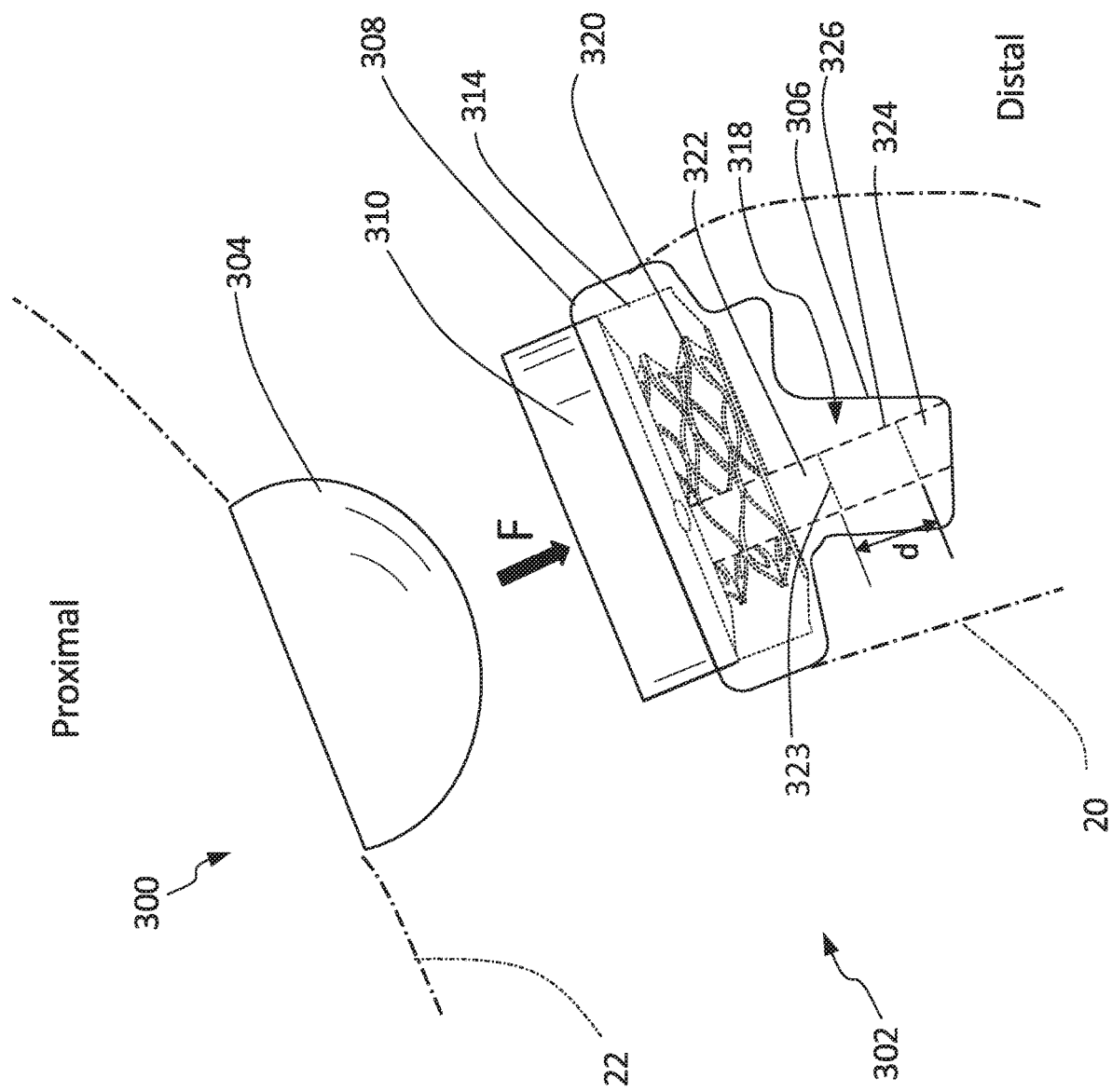
FIG. 3 illustrates an isometric and partial cross-sectional view of another example of a reverse shoulder prosthetic assembly including a sensor, in accordance with at least one example of this disclosure.

FIG. 3 illustrates an isometric view of reverse shoulder 300, which can include humeral component 302 and glenoid component 304. Humeral component 302 can include stem 306, cup 308, articulation component 310, displacement sensor 318, and bias element 320. Cup 308 can include bore 314. Displacement sensor 318 can include rod 322, detector 324, and sensor bore 326. Also shown in FIG. 3 are humerus 20, glenoid 22, force F, distance d, and orientation indicators Proximal and Distal.

Reverse shoulder 300 can be a prosthetic trial assembly for use in a reverse shoulder arthroplasty, which can be connected and can operate similarly to reverse shoulder 100 described in FIG. 1 above. However, reverse shoulder 300 can differ in that reverse shoulder 300 can include displacement sensor 318 and bias element 320.

Bias element 320 can be a biasing device, such as a compression spring, disposed in bore 314. In some examples, bias element can be a poly or multi-turn wave spring. Bias element 320 can engage a distal side of articulation component 310 and a proximal side of cup 308 to bias articulation component 310 in a proximally extended position from humeral component 302.

Displacement sensor 318 can be a sensor assembly configured to produce a displacement signal as a function of a distance, such as distance d between rod 322 and detector 324. Rod 322 can be coupled to a distal side of articulation component 310, extending distally therefrom and terminating at a distal end within bore 326. Being coupled to articulation component 310, rod 322 can be translatable within bore 326, translating proximally and distally as articulation component 310 translates proximally and distally. Because rod 322 is connected to articulation component 310, distance d, measured by displacement sensor 318 directly correlates to a proximity of articulation component 310 and cup 308.

In some examples, rod 322 can include a magnet, such as a permanent magnet, disposed on a distal end of rod 322. In these examples, detector 324 can be a sensor configured to produce a sensor signal as a function of a sensed magnetic field, such as a hall sensor, disposed at a distal termination of bore 326 in stem 306. Detector 324 can be disposed in bore 326 in proximity to rod 322 and can be configured to produce a signal as a function of a detected magnetic field emitted by rod 322. In such cases, the displacement signal produce by detector 324 can be correlated to distance d between rod 322 and detector 324. In some other examples, the displacement signal be generated as a function of a sensed electric field, for example when capacitive displacement sensing is used as displacement sensor 318.

In operation of some examples, glenoid component 304 can be installed on glenoid 22 and humeral component 302 can be installed on humerus 20, similar to reverse shoulder 100, as described in further detail above. Once the trial components, glenoid component 304 and humeral component 302 are installed, a physician can operate humerus 20 relative to glenoid 22, allowing glenoid component 304 to articulate on articulation component 310.

As glenoid component 304 contacts articulation component 310, forces, such as force F, may be transferred between glenoid component 304 and humeral component 302 through articulation component 310. Force F can be transmitted through articulation component 310 and can be applied to bias member 320, compressing bias member 320 between articulation component 310 and cup 308 and forcing articulation component 310 to translate distally. As articulation component 310 translates, so too does rod 322, which translates in bore 326 towards detector 324. As rod 322 translates towards detector 324, distance d becomes smaller. As distance d becomes smaller the magnetic field detected by detector 324 becomes large, which is detected by detector 324. Detector 324 can convert the detected magnetic field into a signal that can be transmitted for collection and analysis.

In continued operation of some examples, force F may be increased or continually applied causing articulation component 310 to continue to translate distally until articulation component 310 bottoms out by contacting a proximal surface of cup 308 or by contacting bias element 320 in a fully compressed state. In continued operation, force F may be removed or reduced below a spring force of bias element 320, allowing bias element 320 to move articulating surface 310 proximally due to the spring force applied by bias element 320 in a direction opposing force F. This can cause distance d to increase as rod 322 translates away from detector 324, where detector 324 can accordingly adjust its displacement signal.

As discussed in FIG. 5 below, the displacement signal can be analyzed (and visualized through a user interface) to allow for a physician to analyze operation of reverse shoulder 300. In some examples, the displacement signal can be converted into a measure of the applied force based on a known spring force of bias element 320.

In operation of some examples, a displacement of articulation portion 310 may not occur. In these cases, an articulation portion 310 of a different height or thickness can be inserted until glenoid component 304 displaces articulation component 310. This process can help in selecting permanent implants or prostheses.

Figure 4:
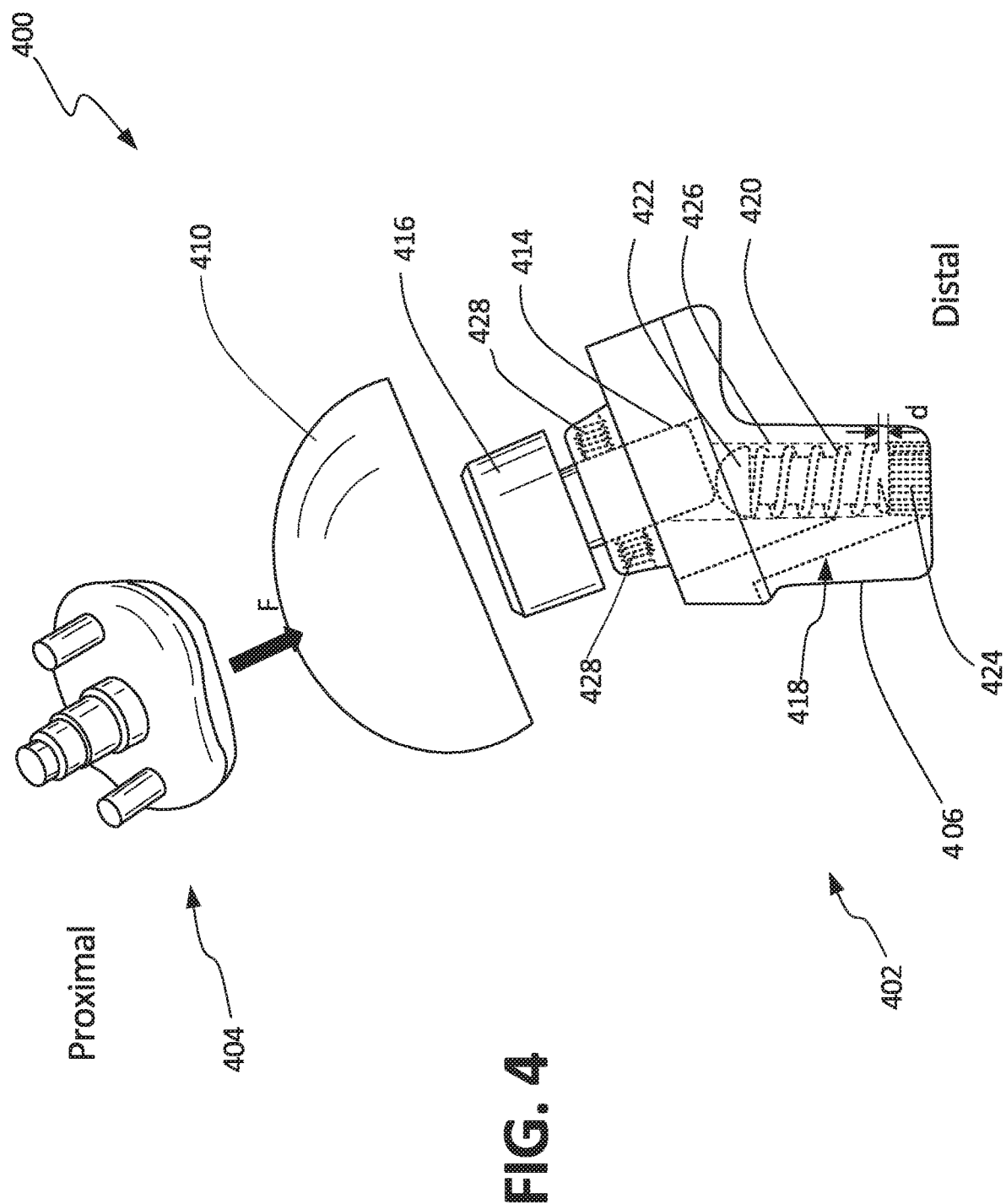
FIG. 4 illustrates an isometric and partial cross-sectional view of another example of an anatomical shoulder prosthetic assembly including a sensor, in accordance with at least one example of this disclosure.

FIG. 4 illustrates an isometric view of anatomical shoulder 400, which can include humeral component 402 and glenoid component 404. Humeral component 402 can include stem 406, articulation component 410, adapter 216, displacement sensor 418, bore 426, and set screws 428. Displacement sensor 418 can include bias element 420, rod 422, and detector 424. Also shown in FIG. 4 are force F and orientation indicators Proximal and Distal.

Anatomical shoulder 400 can be a prosthetic trial assembly for use in a reverse shoulder arthroplasty, which can be connected and can operate similarly to anatomical shoulder 200 described in FIG. 2 above. However, anatomical shoulder 400 can differ in that anatomical shoulder 400 can include displacement sensor 418.

Displacement sensor 418 can be a sensor assembly configured to produce a displacement signal as a function of a distance, such as distance d between rod 422 and detector 424. Rod 422 can be disposed within bore 426 and partially within bore 414 so that a proximal termination of rod 422 can engage a distal termination of adapter 416, rod 422 terminating at a distal end within bore 426. Being engaged to adapter 416, rod 422 can be translatable within bore 426, translating proximally and distally as articulation component 410 (and therefore adapter 416) translates proximally and distally.

Bias element 420 can be a biasing device, such as a compression spring, disposed around rod 422 within bore 426. In some examples, bias element can be a coil spring wrapped around rod 422. Bias element 420 can engage a distal side of adapter 416 and a proximal side of detector 424 to bias adapter 416 and articulation component 410 in a proximally extended position from humeral component 402. Set screws 428 can retain adapter 416, allowing motion of adapter 416, but retaining adapter 416 in bore 414.

In some examples, rod 422 can include a magnet, such as a permanent magnet, disposed on a distal end of rod 422. In these examples, detector 424 can be a sensor configured to produce a sensor signal as a function of a magnetic field, such as a hall sensor, disposed at a distal termination of bore 426 in stem 406. Detector 424 can be disposed in bore 426 in proximity to rod 422 and can be configured to produce a signal as a function of a detected magnetic field emitted by rod 422. In such cases, the displacement signal produce by detector 424 can be correlated to distance d between rod 422 and detector 424. In some other examples, the displacement signal be generated as a function of a sensed electric field, for example when capacitive displacement sensing is used as displacement sensor 418.

In operation of some examples, glenoid component 404 can be installed on a glenoid, and humeral component 402 can be installed on a humerus, similar to anatomical shoulder 100, as described in further detail above.

Once the trial components, glenoid component 404 and humeral component 202 are installed, a physician can operate humerus 20 relative to glenoid 22, allowing glenoid component 404 to articulate on articulation component 310.

As glenoid component 404 contacts articulation component 410, forces, such as force F, may be transferred between glenoid component 404 and humeral component 404 through articulation component 410. Force F can be transmitted through articulation component 410 to adapter 416 and can be applied to bias member rod 422 and therefore bias member 420, compressing bias member 420 between a retaining head of rod and detector 424. As force F compresses bias member 420, articulation component 410 can translate along with adapter 416 and rod 422, Rod 422 can translate in bore 426 towards detector 424. As rod 422 translates towards detector 424, distance d becomes smaller. As distance d becomes smaller the magnetic field detected by detector 424 becomes larger as the magnet of rod 422 becomes closer to detector 424. Detector 424 can convert the detected magnetic field into a signal that can be transmitted for collection and analysis.

In continued operation of some examples, force F may be increased or continually applied causing articulation component 410 to continue to translate distally until adapter 416 bottoms out by contacting a proximal surface of humeral component 402 or by contact rod 422 which has bottomed out on detector 424. In continued operation, force F may be removed or reduced below a spring force of bias element 420, allowing bias element 420 to move adapter 416 and therefore articulating surface 410 proximally due to the spring force applied by bias element 420 in a direction opposing force F. This can cause distance d to increase as rod 422 translates away from detector 424, where detector 424 can accordingly adjust its displacement signal.

As discussed in FIG. 5 below, the displacement signal can be analyzed (and visualized through a user interface) to allow for a physician to analyze operation of anatomical shoulder 400.

Figure 5:
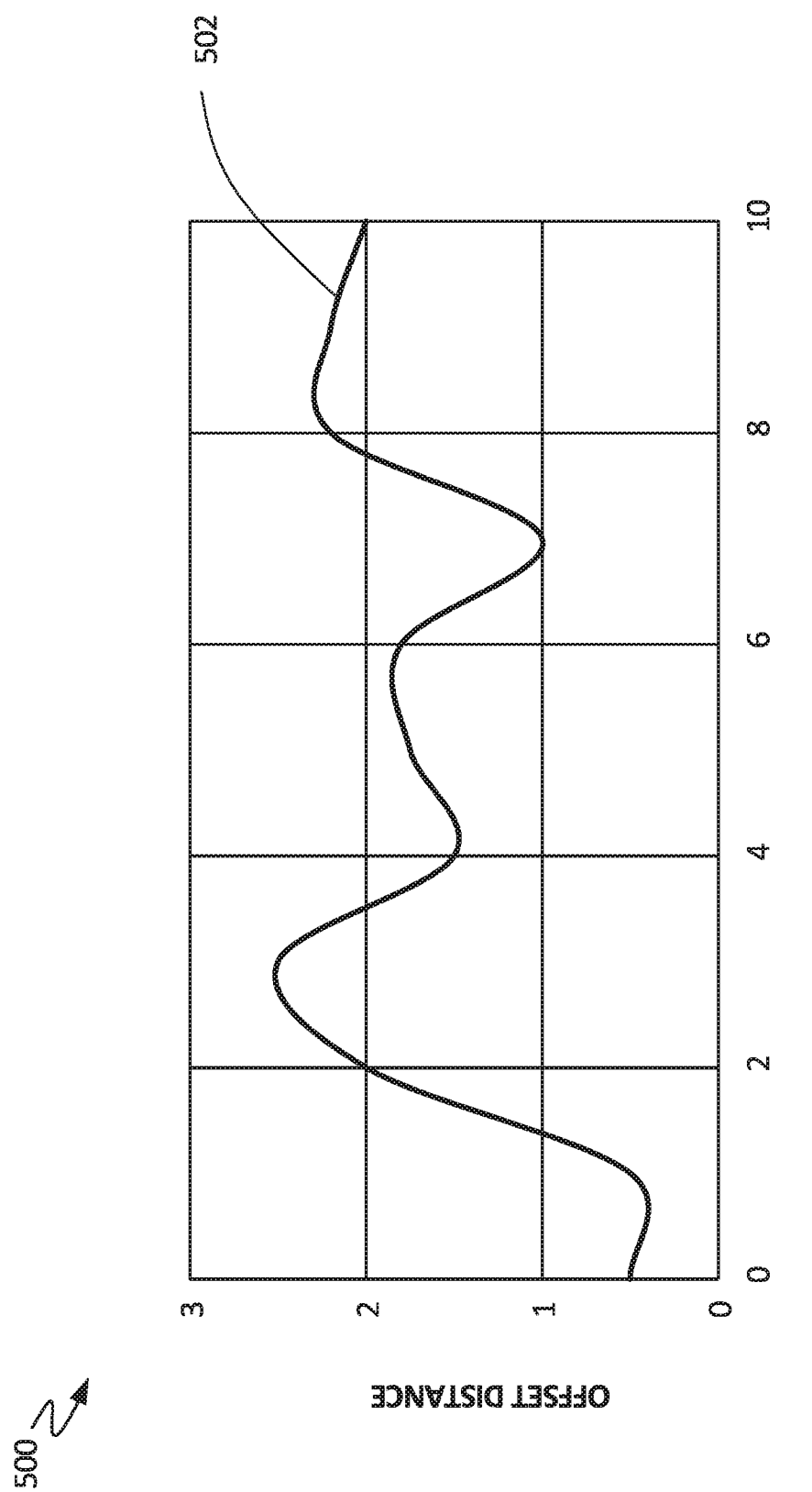
FIG. 5 illustrates a graph produced as a function of a sensor signal, in accordance with at least one example of this disclosure.

FIG. 5 illustrates graph 500 produced as a function of a sensor signal, such as displacement sensor 318 of FIG. 3 or 418 of FIG. 4. Units of time, such as seconds, can be displayed on the x-axis and units of offset distance, such as millimeters, can be displayed on the y-axis. Curve 502 can be a relationship of offset distance over time and is one way to display a quantification of stability of the joint.

In one example, the displacement signal can be used to determine stability of reverse shoulder 300 or anatomical shoulder 400 when installed on glenoid 22 and humerus 20. In some examples, a physician can articulate humerus 20 in the sagittal plane, coronal plane, and transverse plane of a patient, or through an entire range of motion of humerus 20 relative to glenoid 22, including abduction, adduction, flexion, extension, and rotation of humerus 20 relative to glenoid 22.

As humerus 20 is operated, forces, such as force F of FIGS. 3 and 4, may be applied to articulation component 310 or 410, as described above, causing translation of a rod and the production of a displacement signal through detector 324 or 424. Curve 502 shows an example of how displacement can change as a humerus is articulated over time. For example, the offset or distance d starts at approximately 0.5 millimeters at 0 seconds and increases to about 2.5 millimeters at about 3 seconds. The offset distance then decreases and increase through the 10 second diagnostic.

In some examples, a physician can make adjustments to glenoid component 104 and/or humeral component 102 as desired, based on the production of a curve, such as curve 502. For example, a curve of offset over time can be indicative of stability of reverse shoulder 300 or anatomical shoulder 400. For example, a flat curve can indicate that force F is relatively constant, which can indicate that a shoulder is stable. Or, for example, a low offset can indicate that force F is relatively small. These indications from trial components can be used by physicians to analyze the installation of the components of reverse shoulder 300 or anatomical shoulder 400 and determine whether adjustments are necessary or prosthetic components of a different size are necessary. This process can improve the fit and operation of the permanent prosthesis, improving patient quality of life and can improve procedural efficiency, saving cost, in some examples.

Figure 6:
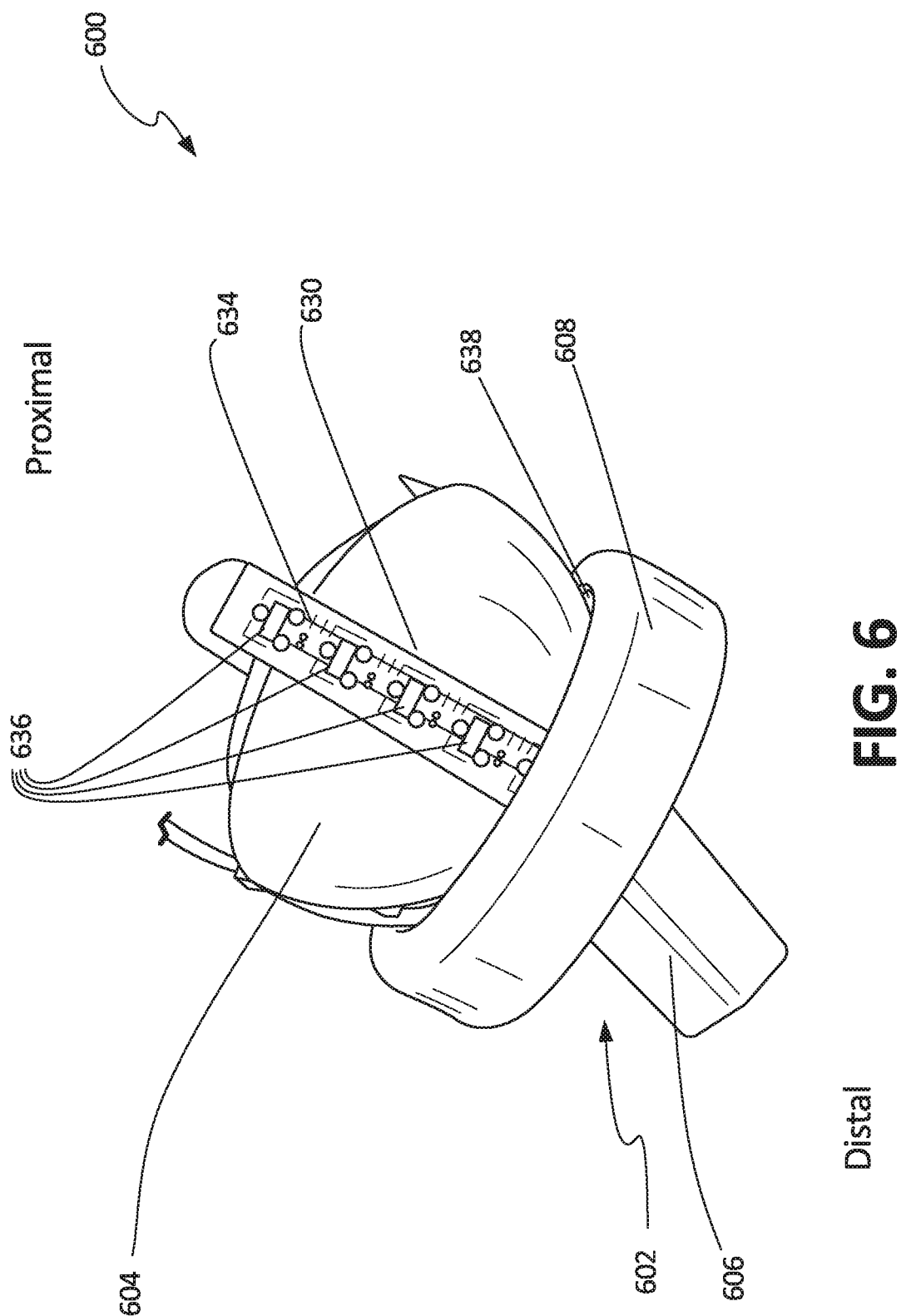
FIG. 6 illustrates an isometric view of a reverse shoulder prosthetic assembly including a plurality of sensors, in accordance with at least one example of this disclosure.

FIG. 6 illustrates an isometric view of reverse shoulder 600, which can include humeral component 602 and glenoid component 604. Humeral component 602 can include stem 606, cup 608, and magnetic ring 638. Glenoid component 604 can include groove 630, printed circuit board (PCB) 634, and proximity sensors 636.

Reverse shoulder 600 can be a prosthetic trial assembly for use in a reverse shoulder arthroplasty, which can be connected and can operate similarly to reverse shoulder 100 described in FIG. 1 above and reverse shoulder 300 described in FIG. 3 above. However, reverse shoulder 600 can differ in that reverse shoulder 600 can include proximity sensors 636.

Groove 630 can be a groove or channel in the surface of glenoid component 604 configured to receive and secure PCB 634. In some examples, groove 630 can extend around a circumference of glenoid component 604. In some examples, groove 630 can extend around only a part of the circumference of glenoid component 604. In some examples, there can be two of grooves 630, each extending along a circumference of glenoid component 604. In some examples, grooves 630 can be oriented about orthogonally to each other.

PCB 630 can be a printed circuit board configured to support and electrically connect the sensors 636 and other electronic components configured to operate sensors 636, such as capacitors and a communication circuit. Sensors 636 can be soldered to or otherwise coupled to PCB 630. PCB 630 can include a non-conductive substrate with an etched copper plate as a laminated layer that can provide the electrical connections of PCB 630, in some examples.

In some examples, sensors 636 can be sensors configured to detect proximity of an object. In some examples, sensors 636 can be sensors that detect magnetic fields, such as hall sensors. Magnetic ring 638 can be disposed in a circumferential groove around an internal surface of cup 608. In some examples, magnetic ring 638 can be comprised of a permanent magnet and in some examples, magnetic ring 638 can be comprised of an electromagnet. When installed, sensors 636 can detect the proximity of magnetic ring 638, which can provide data to a controller or other device for analysis and visualization, as described further below in FIGS. 7A and 7B.

Humeral component can include, though not shown in FIG. 6, a force sensor similar to that of force sensor 112 of FIG. 1 or a displacement sensor, similar to that of displacement sensor 318 of FIG. 3. This can allow reverse shoulder 600 to transmit a force or displacement signal and a plurality of proximity signals for analysis, as described further below.

Figure 7A:
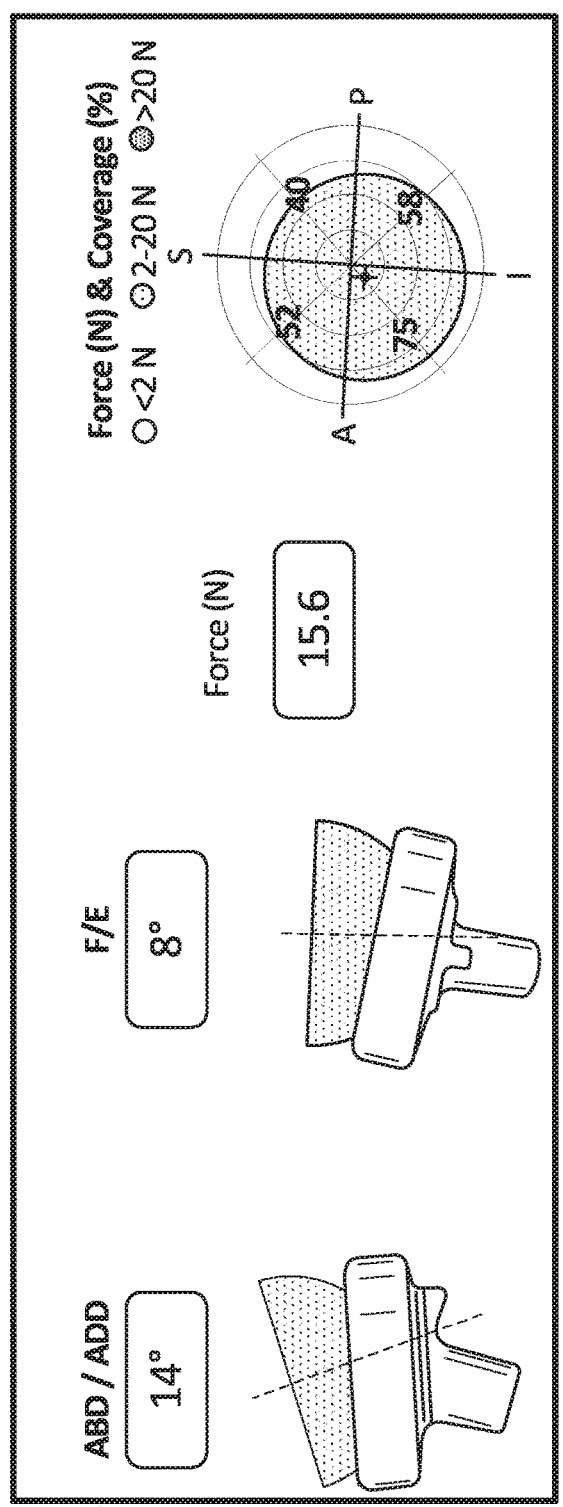
FIG. 7A illustrates a graphic display produced as a function of the plurality of sensors of the reverse shoulder prosthetic assembly such as illustrated in FIG. 4, in accordance with at least one example of this disclosure.
Figure 7B:
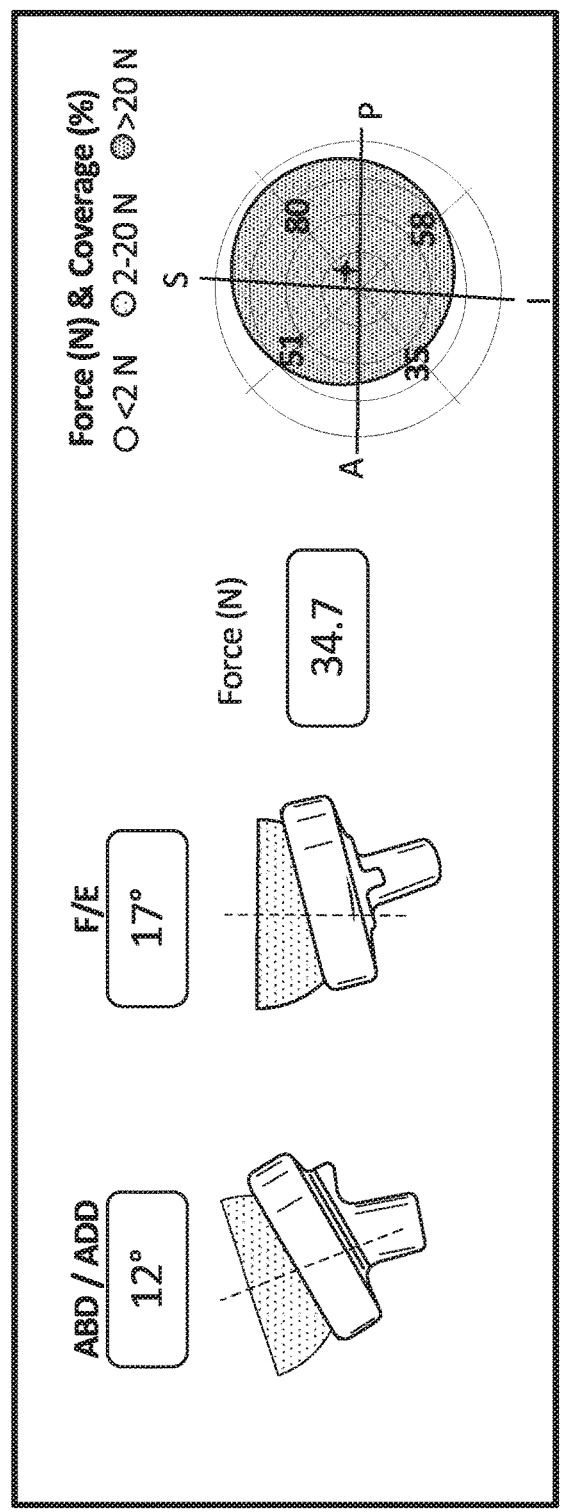
FIG. 7B illustrates another example of a graphic display produced as a function of the plurality of sensors of the reverse shoulder prosthetic assembly such as illustrated in FIG. 4, in accordance with at least one example of this disclosure.

FIG. 7A illustrates a graphic display 700A produced from reverse shoulder 600 where glenoid component 604 is in a first position relative to humeral component 602 and FIG. 7B illustrates a graphic display 700B produced from reverse shoulder 600 where glenoid component 604 is in a second position relative to humeral component 602.

In operation of some examples, glenoid component 604 and humeral component 602 can be installed on a glenoid and humerus, respectively, consistent with the installation of reverse shoulders described above. Thereafter, a physician can articulate the humerus in which humeral component 602 is installed relative to the glenoid. For each position of glenoid component 604 relative to humeral component 602, several sensor signals can be sent from PCB 634 to a controller, which the controller can use to perform analysis and can use to produce a graphic display.

The position of glenoid 604 relative to humeral component 602 can be determined through analyzing the signals received from sensors 636. Because each of sensors 636 is fixed relative to glenoid component 604, but is movable with glenoid component 604 relative to humeral component 602 (and magnetic ring 638), and because magnetic ring 638 is fixed relative to humeral component 602, the sensor signals produced by sensors 636 can be used to precisely determine the position of glenoid component 604 relative to humeral component 602 in three dimensions due to the shape and orientation of the sensor array (the displays 700A, 700B illustrate this by show multiple orthogonal views labeled in a manner meaningful to a physician).

For example, glenoid component 604 can be in a first position relative to humeral component 602, as shown in graphic display 700A. As shown by the ABD/ADD (abduction/adduction) image, glenoid component 604 is approximately 14° off of a neutral position relative to humeral component 602. As shown by the F/E (flexion/extension) image, glenoid component 604 is approximately 8° off of a neutral position relative to humeral component 602. Display 700A also shows the force applied from glenoid component 604 to humeral component 602 as 15.6 Newtons (N) in the first position of glenoid component 604 relative to humeral component 602.

Further, display 700A shows a coverage and force map, illustrating the superior-inferior axis (S/I) and anterior-posterior axis (A/P). A shaded circle is displayed on the map indicating the location of glenoid component 604 relative to humeral component 602. The coverage map offers another visualization of glenoid component 604 relative to humeral component 602 by displaying a percentage of coverage of the glenoid component 604 by the humeral component 602 in each quadrant in the positions shown in the S/I and A/P illustrations. For example, the superior-posterior quadrant of glenoid component 604 is 40% covered by humeral component 602 in the first position. The coverage map can also be color-coded to display a range of forces. For example, the color displayed can be a first color, such as yellow, when a force applied to glenoid component is less than 2 Newtons, a second color, such as green, when the force applied is between 2 and 20 Newtons, and a third color, such as red, when the force applied is greater than 20 Newtons. In the example of display 700A, the map can be shown as green, because the force applied by glenoid component 604 to humeral component 602 is 15.6 Newtons, which is between 2 and 20 Newtons. In some examples, the force ranges can change depending upon application and trial prosthetic devices being used. In some other examples, the quadrants shown in the coverage map can be color-coded according to a coverage percentage for each quadrant.

In some other examples, the coverage map can indicate displacement instead of force. Similarly, display 700A can include, in some other examples, numeral indications of displacement measured by a displacement sensor, such as displacement sensor 318 of FIG. 3.

In operation of some examples, humeral component 604 can be moved to a second position relative to glenoid component 604, as displayed by graphic display 700B of FIG. 7B.

As shown by the ABD/ADD image, in the second position glenoid component 604 is approximately 12° off of a neutral position relative to humeral component 602. As shown by the F/E image, glenoid component 604 is approximately 17° off of a neutral position relative to humeral component 602.

Display 700B also shows the force applied from glenoid component 604 to humeral component 602 as 34.7 Newtons (N). In display 700B the force is shown in a red box, consistent with the color-coding of the coverage map, as described above.

In graphic display 700B, for example, the superior-posterior quadrant of glenoid component 604 is 80% covered by humeral component 602 in the first position. Also, in the example of graphic display 700B, the map can be shown as red, because the force applied by glenoid component 604 to humeral component 602 is 34.7 Newtons.

In operation of some examples, a physician can make adjustments to glenoid component 604 and/or humeral component 602 as desired, based on the production the displayed images, such as graphic images 700A and 700B. For example, a force of 15.6 Newtons when glenoid component 604 is aligned at 14° from neutral ABD/ADD and 8° from neutral F/E may indicate that reverse shoulder 600 is stable in the first position and not in need of adjustments. However, a force of 34.7 Newtons when glenoid component 604 is aligned at 12° from neutral ABD/ADD and 17° from neutral F/E may indicate that reverse shoulder 600 is not stable, for example, large offsets or relative angular positions may indicate a likelihood of impingement. In those conditions, glenoid component 604 and/or humeral component 602 and/or connecting soft tissues may be adjusted, reducing the risk of impingement in the permanent prostheses. These processes can improve the fit and operation of the permanent prostheses, improving patient quality of life and improving procedural efficiency, saving cost, in some examples.

FIG. 8A illustrates an isometric view of anatomical shoulder 800, which can include humeral component 802 and glenoid component 804. Humeral component 802 can include articulation component 810, anterior groove 831, inferior groove 832, posterior groove 833, and superior groove (not visible), anterior PCB 834, inferior PCB 835, posterior PCB 837, superior PCB (not visible), and fasteners 840. Anterior PCB 834 can include anterior proximity sensors 842a, 842b, 842c, 842d, and 842e (not visible). Inferior PCB 835 can include inferior proximity sensors 844a, 844b, 844c, 844d, and 844e (not visible). Posterior PCB 837 can include posterior proximity sensors 846a, 846b, 846c (not visible), 846d (not visible), and 846e (not visible). Glenoid component 804 can include articulation surface 848 (not visible). Also shown in FIG. 8A are orientation indicators Superior, Inferior, Anterior, and Posterior.

Anatomical shoulder 800 can be a prosthetic trial assembly for use in a reverse shoulder arthroplasty, which can be connected and can operate similarly to anatomical shoulder 200 or 400 described 2 above. However, anatomical shoulder 800 can differ in that humeral component 802 can include four PCBs that include proximity sensors, and glenoid component 804 can include articulation surface 848, which can be a magnetic surface. In some examples, the proximity sensors of anatomical shoulder 800 can be arranged in a plus (+) or x pattern, as shown in FIG. 8. In some other examples, the proximity sensors can be arranged in a grid, in multiple concentric circles, and the like.

Anterior groove 831, inferior groove 832, posterior groove 833, and superior groove can be grooves in the surface of articulation component 810, each configured to receive and retain anterior PCB 834, inferior PCB 835, posterior PCB 837, and superior PCB, respectively. Anterior PCB 834, inferior PCB 835, posterior PCB 837, and superior PCB can be printed circuit boards consistent with the description of PCB 634 above. Each of inferior proximity sensors 844a-844e, inferior proximity sensors 844a-844e, posterior proximity sensors 844a-844e, and superior proximity sensors can be proximity sensors, such as hall sensors, consistent with the description of proximity sensors 636 above.

FIG. 8B shows graphic display 850, which can be a graphic display produced on an interface, by a controller, as a representation of the sensor signals produced by the proximity sensors of anatomical shoulder 800.

In operation of some examples, glenoid component 804 and humeral component 802 can be installed on a glenoid and humerus, respectively, consistent with the installation of anatomical shoulders described above. Thereafter, a physician can articulate the humerus in which humeral component 802 is installed relative to the glenoid. For each position of glenoid component 804 relative to humeral component 802, sensor signals can be transmitted from anterior PCB 834, inferior PCB 835, posterior PCB 837, and superior PCB to a controller, which the controller can use to perform analysis and can use to produce a graphic display, such as graphic display 850.

Graphic display 850 can include humeral perimeter indicator 852, which is a visual representation of the perimeter of humeral component 804. Graphic display 850 can also include anterior proximity displays 854, inferior proximity displays 856, posterior proximity displays 858, and superior proximity displays 860. Anterior proximity displays 854 correspond to the signal sensor produced by each of anterior proximity sensors 842a-842e, inferior proximity displays correspond to the sensor signal produced by each of inferior proximity sensors 844a-844e, posterior proximity displays 858 correspond to the sensor signal of each of posterior proximity sensors 846a-846e, and superior proximity displays 860 each correspond to the sensor signals of superior proximity sensors.

Proximity displays 854, 856, 858, and 860 can be configured to display several colors based on the proximity of articulation portion 848 of glenoid component 804 to each of the proximity sensors. For example, a first color, such as red, can be used to indicate articulation portion 848 is not covering or nearby the proximity sensor. A second color, such as green, can indicate articulation portion 848 is covering the proximity sensor. A third color, such as blue can be used to indicate articulation portion 848 is nearby, but not covering, the proximity sensor.

In the example shown in FIG. 8B, the positions of glenoid component 804 and humeral component 802 as shown in FIG. 8A are graphically represented by graphic display 850. More specifically, as shown in FIG. 8A, anterior proximity sensor 842e, inferior proximity sensor 844e, and posterior proximity sensors 846d and 846e are covered by glenoid component 804. Some of superior proximity sensors are also covered by glenoid component 804 in FIG. 8A, but it is not clearly visible in FIG. 8A. Because of the coverage of these sensors by glenoid component 804 and articulation portion 848, anterior proximity sensor 854 corresponding to anterior proximity sensor 842e is shown as green, as are inferior proximity sensor 844e, posterior proximity sensors 846d and 846e, and two of superior proximity indicators 860.

The sensors not covered by articulation portion 848 are shown in graphic display 850 as being either red or blue. The proximity sensors adjacent to articulation portion 848, such as anterior proximity sensor 842d, inferior proximity sensor 844d, and posterior proximity sensor 846c (not clearly visible in FIG. 8A), are shown by blue indicators. The proximity sensors not adjacent to articulation portion 848, such as anterior proximity sensors 842a-842c are shown as red on graphic display 850.

This three color, color-coded display can provide a visual representation of the orientation and position of glenoid component 804 relative to humeral component 802. Such a representation may be useful when using trial components during a procedure, as the interaction between the trial components may be difficult to visualize once installed. In some examples, a physician can make adjustments to glenoid component 804 and/or humeral component 802 as desired based on the analysis derived from graphic display 850. In some examples, a physician can use the analysis derived from the coverage map of graphic display 850 to select permanent humeral and glenoid prosthetic components. Therefore, the visualization provided to a physician during a procedure can improve the fit and operation of the permanent prosthesis, improving patient quality of life and can improve procedural efficiency, saving cost, in some examples.

In some examples, anatomic shoulder 800 can be configured to produce displays such as those of FIGS. 7A and 7B, including a coverage map, alignment angles, and force and/or displacement indications.

FIG. 9A illustrates an isometric reverse shoulder 900 and FIG. 9B illustrates an exploded isometric view of humeral component 902 of reverse shoulder 900. FIGS. 9A and 9B are discussed concurrently.

Reverse shoulder 900 can include humeral component 902. Humeral component 902 can include base 961, articulation component 910, rim 962, and impingement sensors 964. Articulation component 910 can include threaded portion 966. Rim 962 can include impingement bores 968.

Reverse shoulder 900 can be a prosthetic trial assembly for use in a reverse shoulder arthroplasty, which can be connected and can operate similarly to reverse shoulder 100 described in FIG. 1 above, reverse shoulder 300 described in FIG. 3 above, and reverse shoulder 600 of FIG. 6 above. However, reverse shoulder 800 can differ in that reverse shoulder 800 can include impingement sensors 964 distributed around a perimeter of a proximal side of base 961 engaging a distal side of rim 962, and extending into impingement bores 968. Impingement sensors 964 can be configured to detect a force applied to rim 962 by a humeral component, as described further below.

Reverse shoulder 900 also differs in that articulation component 910 includes threaded portion 966, which can threadably engage a portion of base 961 to couple and secure articulation component 910 to base 961. Base 961, rim 962, and articulation component 910 can include scallops along an outer edge or perimeter that can be configured to be engaged by a tool for removal, insertion, tightening, loosening, and the like.

Figure 10:
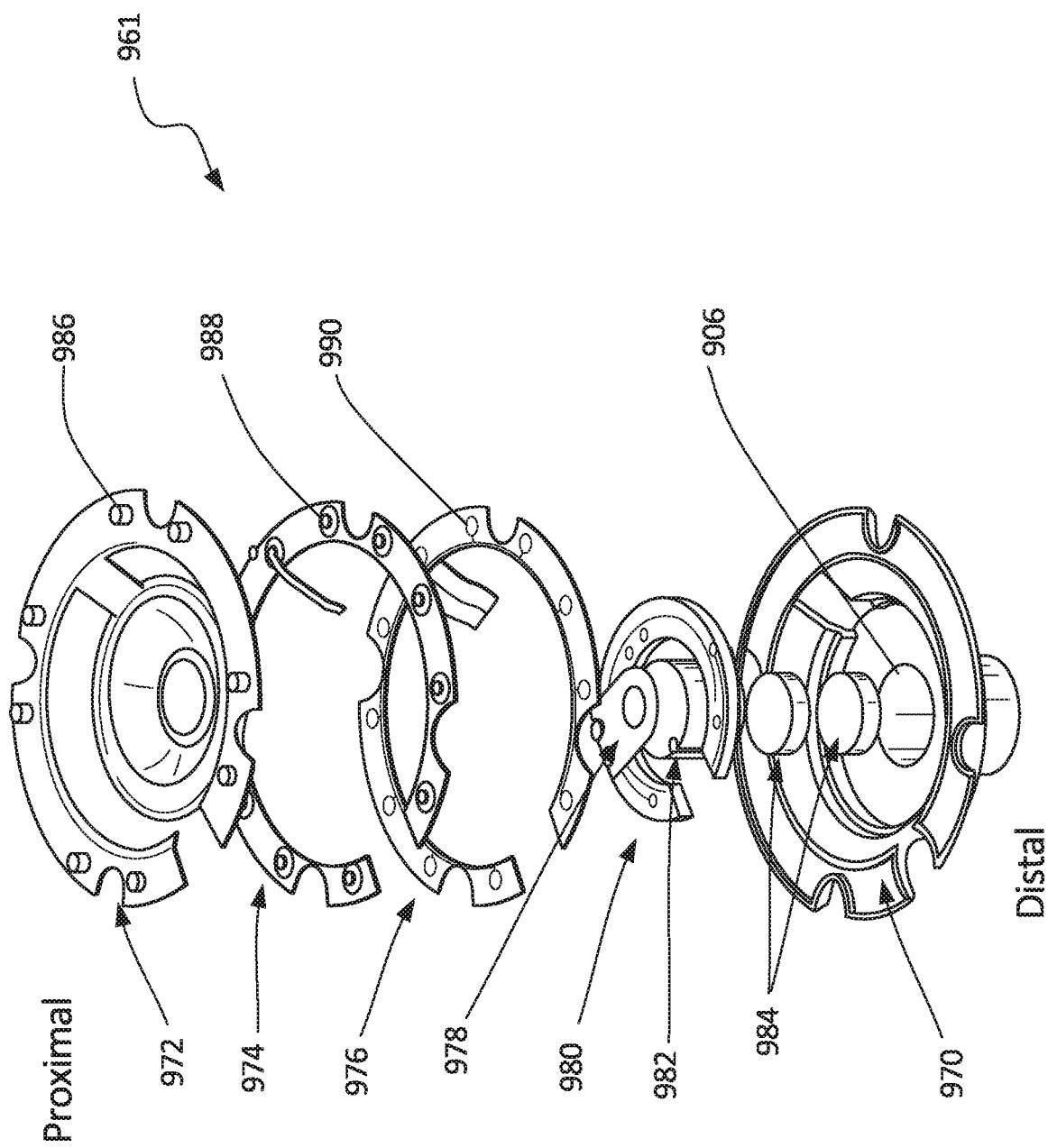
FIG. 10 illustrates an exploded view of a reverse shoulder prosthetic assembly, in accordance with at least one example of this disclosure.

FIG. 10 illustrates an exploded isometric view of base 961 of reverse shoulder 900. Base 961 includes stem 906, base plate 970, cap 972, deflection plate 974, impingement PCB 976, force sensor 978, PCB 980, central support 982, and capacitors 984. Cap 972 can include impingement protrusions 986. Deflection plate 974 can include deflectors 988. Impingement PCB 976 can include contacts 990.

Base plate 970 can be a rigid component configured to support the components of base 961. Base plate 970 can be comprised of biocompatible materials, such as titanium alloys, stainless steel alloys, cobalt/chromium, and the like. Base plate 970 can include step 906, which can extend distally from base plate 970, and can include a cavity, which can receive capacitors 984 and central support 982.

Capacitors 984 can be batteries and central support can be a conductive member configured to connect capacitors 984 to PCB 980 and/or force sensors 978 and/or flexible PCB 976. PCB 980 can be a substantially circular PCB consistent with the PCBs described above. Flexible PCB 976 can be a substantially circular PCB consistent with the PCBs described above, but can be comprised of a flexible substrate. Flexible PCB 976 can be electrically connected to PCB 880 and/or force sensor 978 and deflection plate 974.

Force sensor 978 can be a load cell or force sensor, consistent with the force sensors described above, such as force sensor 112. Force sensor 978 can be disposed between a distal portion of cover plate 972 and central support 982. Force sensor 978 can be electrically connected to PCB 980 and/or flexible PCB 976.

Deflection plate 974 can be a conductive plate including deflectors 988, which are distally deflectable to contact contactors 990 of flexible PCB 976. Each of deflectors 988 can be aligned with one of contactors 990 on a distal side and one of impingement protrusions 986 on a proximal side of deflector plate 974.

Cover plate 972 can be comprised of a flexible material, such as a plastic, rubber, a flexible metal alloy, and the like. Cap 972 can be formed of a shape to cover the components of base 961 when a distal side of cap 972 mates to a proximal portion of base plate 970 to enclose the contents of base 961.

In operation of one example, humeral component 902 can be secured as a trial into the humerus of a patient and a glenoid component can be secured to the glenoid of a patient. Then, a physician can operate the humerus relative to the glenoid, allowing the glenoid component to articulate on articulation component 910. This interaction between the glenoid component and articulation component 910 can transmit a force to articulation component 910, which can be detected by force sensor 978 and converted to a force signal, which PCB 980 can transmit for analysis.

Additionally, as the glenoid component moves relative to humeral component 902, the glenoid component may impact rim 962. When rim is impacted by the glenoid component, the forces are transferred through rim 962 and into impingement protrusions 986. Impingement protrusions 986 can transfer that force to deflectors 988. When the force transferred to any one of deflectors 988 is sufficiently large, deflectors 988 can deflect to contact contacts 990. This can produce a signal at any of contacts 990 to indicate a force applied on rim 962. Each of contacts 990 can transmit an individual signal, or a single signal can be transmitted. These impingement sensor signals can be used to detect impingement between the glenoid component and humeral component 902.

As discussed above, each the sensor signals can be analyzed (and visualized through a user interface) to allow for a physician to analyze operation of humeral component 902. In one example, the force signal can be used to determine stability of the glenoid component and humeral component 902 as they are installed on the glenoid and the humerus, respectively, and impingement signals can be used to determine impingement between the glenoid component and humeral component 902. Because impingement sensors 964 are disposed around a perimeter of rim 962 and can produce individual signals, an impingement force may be located by analyzing the impingement signals.

In some examples, a physician can make adjustments to the glenoid component and/or humeral component 902 as desired based on the analysis derived from the force signal and the impingement signals. In some examples, a physician can use the analysis derived from the signals to select permanent humeral and glenoid prosthetic components. This selection process can improve the fit of the permanent prosthesis, improving patient quality of life and can improve procedural efficiency, saving cost, in some examples.

Figure 11:
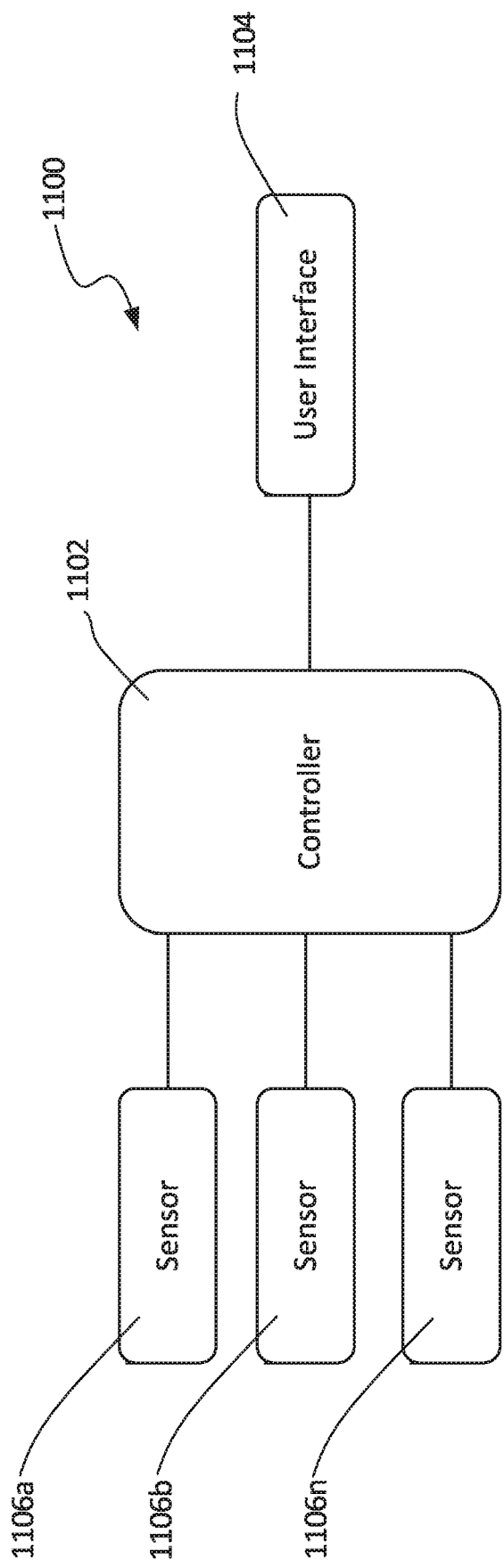
FIG. 11 illustrates schematic showing how the sensors of a shoulder prosthetic can be connected, in accordance with at least one example of this disclosure.

FIG. 11 illustrates schematic showing how sensors 1106a, 1106b, and 1106n of a shoulder prosthetic, such as reverse shoulders 100, 300, 600, and 900, and anatomical shoulders 200, 400, and 800 can be connected, in accordance with at least one example of this disclosure.

In some examples, sensors 1106a-1106n can be connected to controller 1102 through wired connections, in some examples, and through wireless connections in other examples. Controller 1102 can also connect to user interface 1104 via wired or wireless connections.

In some examples, sensors 1106a-1106n can be one, two, three, four, five, ten, or more sensors. Sensors 1106a-1106n can be any sensor consistent with FIGS. 1-10. Controller 1102 can be any computing device, such as a handheld computer, for example, a smart phone, a tablet, a laptop, a desktop computer, or any other computing device including a processor and wireless communication capabilities. User interface 1104 can be any display and/or input device. For example, user interface can be a monitor, keyboard, and mouse in one example. In other examples, user interface 1104 can be a touch screen display. In yet another example, user interface 1104 can provide only a display for controller 1102. Controller 1102 and user interface 1104 can include machine readable medium. The terms "machine readable medium" may include any medium that is capable of storing, encoding, or carrying instructions for execution by the device and that cause the device to perform any one or more of the techniques of the present disclosure, or that is capable of storing, encoding or carrying data structures used by or associated with such instructions. Non-limiting machine readable medium examples may include solid-state memories, and optical and magnetic media. Specific examples of machine readable media may include: non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; and CD-ROM and DVD-ROM disks.

Figure 12:
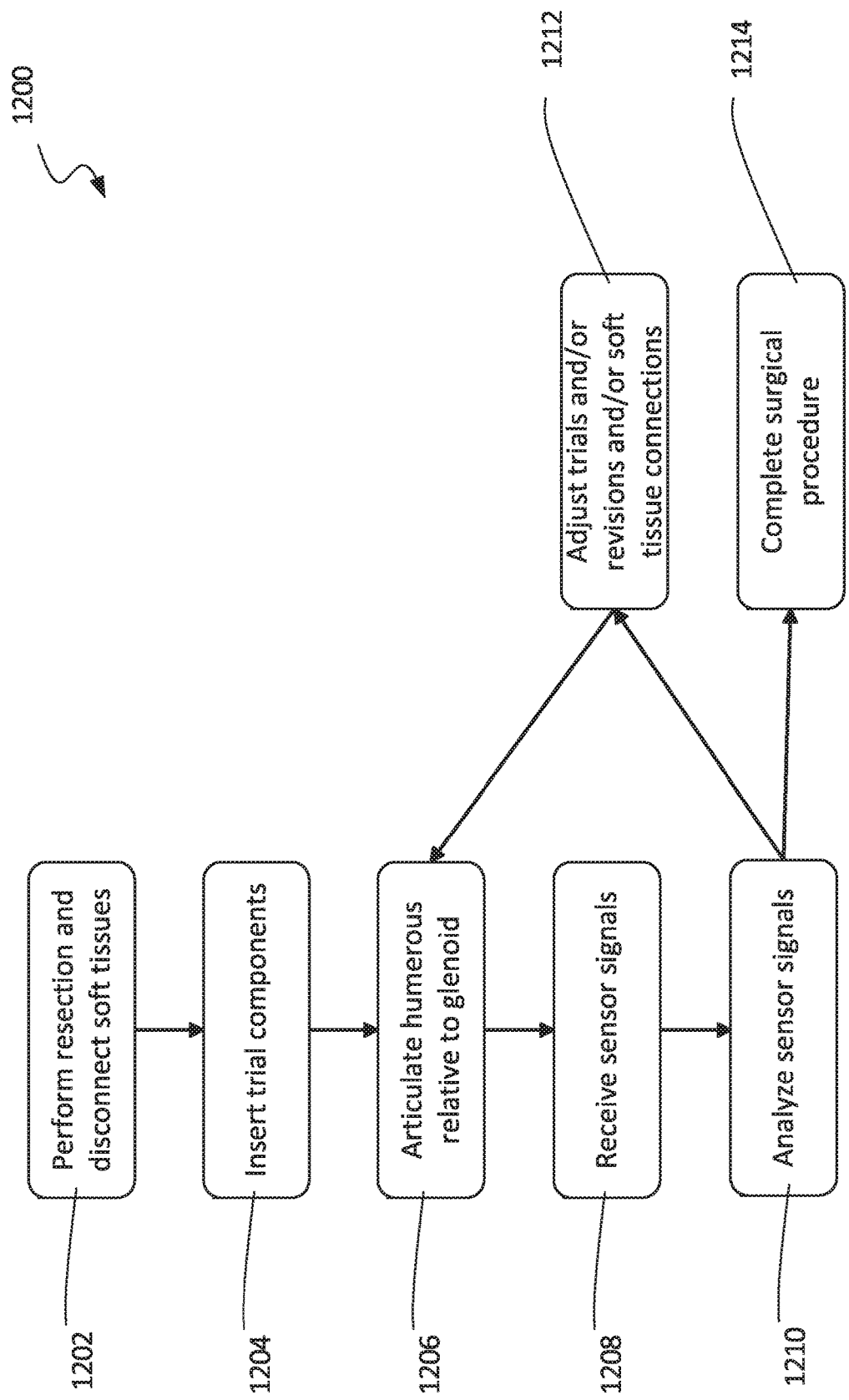
FIG. 12 illustrates a schematic view of a method of using the systems of the present disclosure, in accordance with at least one example of this disclosure.

FIG. 12 illustrates method 1200 of using the devices and systems described above, in accordance with at least one example of this disclosure. The steps or operations of method 1200 are illustrated in a particular order for convenience and clarity; many of the discussed operations can be performed in a different sequence or in parallel without materially impacting other operations. Method 1200 as discussed includes operations performed by multiple different actors, devices, and/or systems. It is understood that subsets of the operations discussed in method 1200 attributable to a single actor, device, or system could be considered a separate standalone process or method. At step 1202, the method 1200 can begin with resections of bone, such as from the humerus and the scapula. Soft tissue can also be moved and disconnected at step 1202, and other preparations to the bones and soft tissues may be made. At step 1204, the trial components, such as glenoid components and humeral components consistent with those described above, can be inserted into the humerus and glenoid.

Thereafter, at step 1206, the physician can articulate the humerus relative to the glenoid, where forces may be transferred between the glenoid component and humeral component, as described above. The forces may be detected through sensors within either or both of the glenoid and humeral components, where the sensors can produce and transmit signals as a function of the sensed forces. At step 1208, the sensors signals can be received at a controller, which can analyze the signals at step 1210. The analysis may be displayed through graphic images, and can enable additional analysis. Based on the analysis, the surgical procedure may be completed at step 1214. If however, it is determined that the trial components, bones, or soft tissues need adjustment, these adjustments may be performed at step 1212. Therefore, steps 1206-1210 can be repeated until it is determined that the trial components and tissue connections are adequate, at which time step 1214 can be performed. Step 1214 can include removing trial components, inserting permanent components, reconnecting soft tissues, and closing the incision.

This method offers the benefit of providing measurement data from trial components that can be used to determine the quality of the proposed connection and the adequacy of the selected implant components. These methods can improve the efficiency of the procedure and can improve the longevity of the implant, by reducing potentially damaging forces from being transferred between the implant components.

Figure 13:
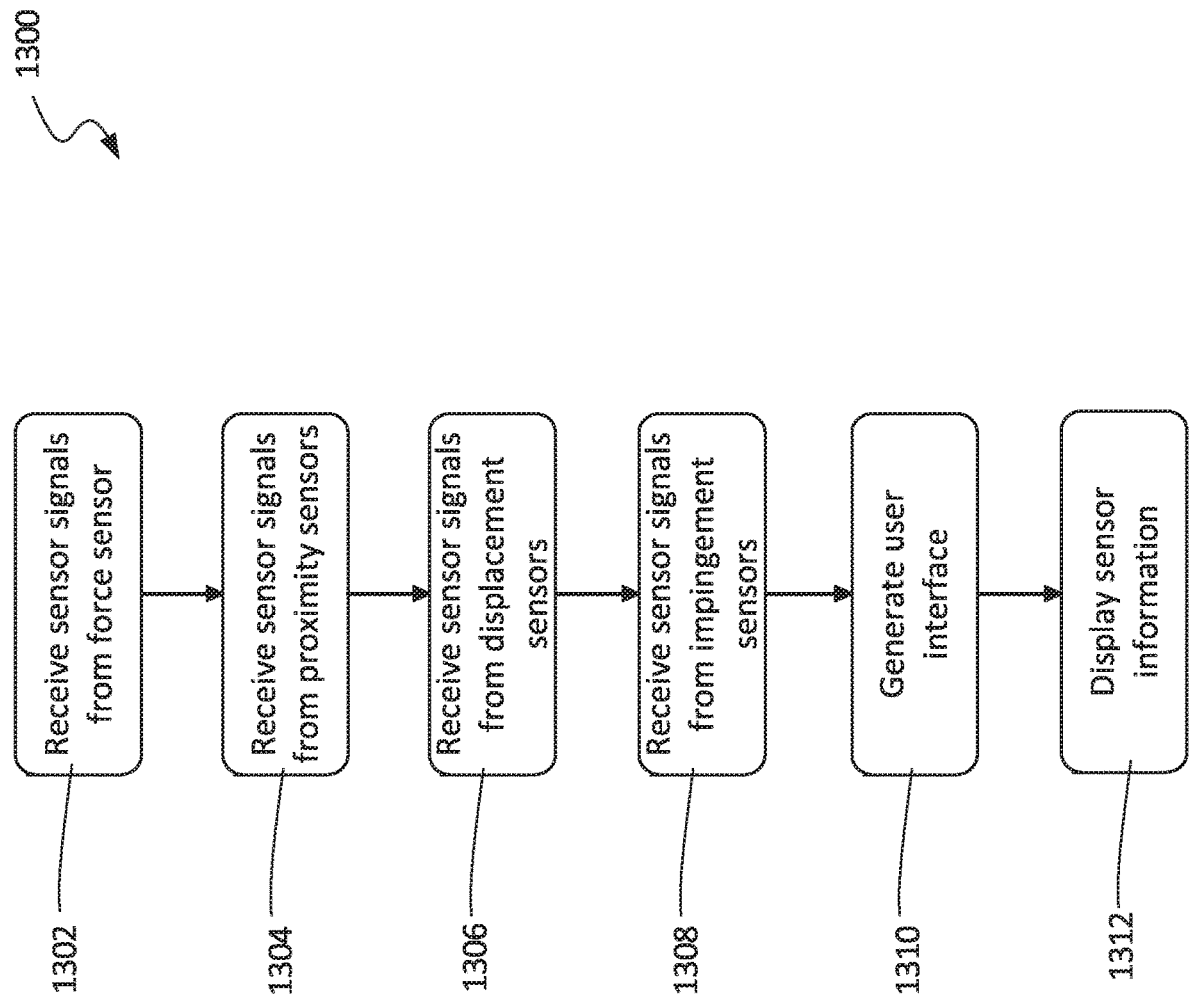
FIG. 13 illustrates a schematic view of another method of using the systems of the present disclosure, in accordance with at least one example of this disclosure.

FIG. 13 illustrates method 1300 of using the devices and systems described above, in accordance with at least one example of this disclosure. The steps or operations of method 1300 are illustrated in a particular order for convenience and clarity; many of the discussed operations can be performed in a different sequence or in parallel without materially impacting other operations. Method 1300 as discussed includes operations performed by multiple different actors, devices, and/or systems. It is understood that subsets of the operations discussed in method 1300 attributable to a single actor, device, or system could be considered a separate standalone process or method. At step 1302, the method 1300 can begin with receiving sensor signals from a force sensor, such as from force sensor 112 of FIG. 1, for example. At step 1304, proximity sensor signals can be received from proximity sensors, such as proximity sensors 636 of FIG. 6, for example. At step 1306, displacement sensor signals can be received from displacement sensors, such as displacement sensor 318 of FIG. 3, for example. At step 1308, impingement sensor signals can be received from impingement sensors, such as impingement sensors 964 of FIG. 9B, for example. Such signals can be received by controller 1102, for example, to produce a graphic display using a user interface, such as user interface 1104, at step 1310. At step 1312, the user interface can display a graphic image using the force sensor signals, proximity sensor signals, and/or displacement sensor signals. For example, the user interface can display graphic images such as those of FIGS. 5, 7A, 7B, and 8B.

Method examples described herein may be machine or computer-implemented at least in part. Some examples may include a computer-readable medium or machine-readable medium encoded with instructions operable to configure an electronic device to perform methods as described in the above examples. An implementation of such methods may include code, such as microcode, assembly language code, a higher-level language code, or the like. Such code may include computer readable instructions for performing various methods. The code may form portions of computer program products. Further, in an example, the code may be tangibly stored on one or more volatile, non-transitory, or non-volatile tangible computer-readable media, such as during execution or at other times. Examples of these tangible computer-readable media may include, but are not limited to, hard disks, removable magnetic disks, removable optical disks (e.g., compact disks and digital video disks), memory cards or sticks, random access memories (RAMs), read only memories (ROMs), and the like.

Additional Notes The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) can be used in combination with each other. Other examples can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above detailed description, various features can be grouped together to streamline the disclosure. This should not be interpreted as intending that an unclaimed disclosed feature is essential to any claim. Rather, inventive subject matter can lie in less than all features of a particular disclosed example. Thus, the following claims are hereby incorporated into the detailed description as examples or embodiments, with each claim standing on its own as a separate example, and it is contemplated that such examples can be combined with each other in various combinations or permutations. The scope of the invention should be determined with reference to the appended claims, along with the full scope of equivalents to which such claims are entitled.

The invention claimed is:

1. A shoulder arthroplasty trial assembly for a human shoulder comprising:
   a first implant securable to a first bone; and
   a second implant securable to a second bone, the second implant comprising:
   a body;
   a stem extending from the body, the stem insertable into the second bone;
   a cup coupled to the body opposite the stem;
   an articulation component disposed entirely within the cup to create a concave articulation surface opposite the stem, the articulation component articulable with the first implant;
   a biasing element connected to the body and the articulation component, the biasing element configured to bias the articulation component to a position at least partially extended from the cup; and
   a sensor connected to the articulation component and configured to monitor a condition of the second implant and produce a sensor signal as a function of the condition that is indicative of stability of the shoulder,
   wherein the biasing element is disposed within the cup and biases the articulation component outwardly from the cup.

2. The arthroplasty trial assembly of claim 1, wherein the articulation component is translatable relative to the body and the sensor is configured to produce the sensor signal as a function of a position of the articulation component relative to the body.

3. The arthroplasty trial assembly of claim 1, wherein the sensor is configured to produce the sensor signal as a function of a force applied to the second implant by the first implant.

4. The arthroplasty trial assembly of claim 1, wherein the sensor is disposed on an articulation surface of the articulation component and is configured to produce the sensor signal as a function of the proximity of the first implant to the second implant.

5. The arthroplasty trial assembly of claim 4, wherein the sensor is a hall sensor and, wherein the first implant includes a magnet disposed on a contact surface of the first implant, the magnet configured to interact with the hall sensor.

6. A shoulder arthroplasty trial assembly comprising:
   a first implant securable to a first bone; and
   a second implant securable to a second bone, the second implant comprising:
   a body;
   a stem extending from the body, the stem insertable into the second bone;
   a cup coupled to the body opposite the stem;
   an articulation component disposed entirely within the cup to create a concave articulation surface opposite the stem, the articulation component translatable relative to the body, and the articulation component articulable with the first implant;
   a biasing element connected to the body and the articulation component, the biasing element configured to bias the articulation component to a position at least partially extended from the cup; and
   a displacement sensor connected to the articulation component and configured to produce a displacement signal as a function of translation of the articulation component relative to the body,
   wherein the biasing element is disposed within the cup and biases the articulation component outwardly from the cup.

7. The assembly of claim 6, further comprising:
   a rod disposed in a bore of the body, the rod connected to the articulation component, the rod biased to an extended rod position by the biasing element, and the rod including a magnet disposed at a second end of the rod, the magnet configured to interact with the displacement sensor.

8. The assembly of claim 7, wherein the sensor produces the signal as a function of the distance between the magnet and the sensor.

9. The assembly of claim 6, wherein the biasing element is a poly wave spring.

10. The assembly of claim 9, further comprising:
a rod coupled to the articulation component at a first end of the rod, the rod extending from the articulation component toward the stem, and the rod including a magnet disposed at a second end of the rod, the magnet configured to interact with the displacement sensor.

* * * * *